US010394517B2

(12) United States Patent
Watanabe et al.

(10) Patent No.: US 10,394,517 B2
(45) Date of Patent: Aug. 27, 2019

(54) CONTROL METHOD, CONTROLLER, AND DEVICE

(71) Applicant: Panasonic Intellectual Property Corporation of America, Torrance, CA (US)

(72) Inventors: Kazuhiro Watanabe, Osaka (JP); Tomohiro Tsuda, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 99 days.

(21) Appl. No.: 15/419,108

(22) Filed: Jan. 30, 2017

(65) Prior Publication Data

US 2017/0235542 A1 Aug. 17, 2017

(30) Foreign Application Priority Data

Feb. 12, 2016 (JP) ................................ 2016-025036

(51) Int. Cl.
*G06F 3/16* (2006.01)
*A61B 5/00* (2006.01)
(Continued)

(52) U.S. Cl.
CPC ............ *G06F 3/165* (2013.01); *A61B 5/0205* (2013.01); *A61B 5/113* (2013.01); *A61B 5/1116* (2013.01); *A61B 5/1123* (2013.01); *A61B 5/4809* (2013.01); *A61B 5/721* (2013.01); *A61B 5/7214* (2013.01); *A61B 5/0022* (2013.01);
(Continued)

(58) Field of Classification Search
CPC ... A61B 5/0022; A61B 5/0024; A61B 5/0205; A61B 5/0507; A61B 5/0816; A61B 5/1116; A61B 5/1123; A61B 5/113; A61B 5/4809; A61B 5/6892; A61B 5/721; A61B 5/7214; A61B 5/7235; A61B 2562/0247;
(Continued)

(56) References Cited

U.S. PATENT DOCUMENTS

2009/0051550 A1* 2/2009 Sasaki .................. A61B 5/0205
340/575
2011/0010014 A1* 1/2011 Oexman ............. A47C 27/061
700/276

(Continued)

FOREIGN PATENT DOCUMENTS

JP 2015-015159 1/2015

*Primary Examiner* — Hemant S Patel
(74) *Attorney, Agent, or Firm* — Greenblum & Bernstein, P.L.C.

(57) ABSTRACT

A method of controlling a device located in a predetermined space includes: obtaining sleep information of a person present in a first space from a biological sensor disposed in the first space, the sleep information indicating a sleep state of the person and the first space includes a first device; determining, by a processor, a first sound volume to be set for the first device based on a first database indicating a correspondence between the sleep state and a target sound volume of a corresponding device, the target sound volume of the corresponding device being a predetermined sound volume which does not awake a sleeping person at the sleep state and still be heard by an awake person; and transmitting, to the first device, a first command for setting the first sound volume in the first device as a sound volume upper-limit value.

20 Claims, 27 Drawing Sheets

(51) Int. Cl.

| | |
|---|---|
| ***A61B 5/0205*** | (2006.01) |
| ***A61B 5/11*** | (2006.01) |
| ***A61B 5/113*** | (2006.01) |
| *A61B 5/05* | (2006.01) |
| *A61B 5/08* | (2006.01) |

(52) U.S. Cl.
CPC ........... *A61B 5/0024* (2013.01); *A61B 5/0507* (2013.01); *A61B 5/0816* (2013.01); *A61B 5/6892* (2013.01); *A61B 5/7235* (2013.01); *A61B 2562/0247* (2013.01); *A61B 2562/0261* (2013.01); *G06F 2212/1721* (2013.01)

(58) Field of Classification Search
CPC ............. A61B 2562/0261; G06F 3/165; G06F 2212/1721
USPC ........................................................... 700/94
See application file for complete search history.

(56) References Cited

U.S. PATENT DOCUMENTS

| | | | | |
|---|---|---|---|---|
| 2014/0116440 | A1* | 5/2014 | Thompson ............. | A61B 5/087 128/204.23 |
| 2015/0164238 | A1* | 6/2015 | Benson .................. | G16H 50/30 340/540 |
| 2015/0302722 | A1* | 10/2015 | Berezhnyy ......... | A61B 5/04012 340/565 |
| 2016/0015184 | A1* | 1/2016 | Nunn ..................... | A47C 27/10 700/282 |
| 2016/0015314 | A1* | 1/2016 | Dusanter .............. | A61B 5/4812 600/301 |
| 2016/0174723 | A1* | 6/2016 | Chan ...................... | A47C 21/00 454/339 |
| 2017/0213450 | A1* | 7/2017 | Park ................... | A61B 5/02416 |
| 2017/0347187 | A1* | 11/2017 | Haberkern ............. | H04R 1/345 |

* cited by examiner

| DEVICE ID (501) | IP ADDRESS (502) | DEVICE CLASS (503) | IDENTIFIER (504) | PROPERTY 1 (INSTALLATION LOCATION) (511) | PROPERTY 2 (OPERATION STATE) (512) | PROPERTY 3 (SLEEP STATE/ILLUMINANCE) (513) | PROPERTY 4 (ILLUMINANCE UPPER LIMIT) (514) | PROPERTY 5 (SOUND VOLUME) (515) | PROPERTY 6 (SOUND VOLUME UPPER LIMIT) (516) | ... |
|---|---|---|---|---|---|---|---|---|---|---|
| TV1 | 192.168.100.2 | TELEVISION | 0x060201 | 2F MAIN BEDROOM | OFF | 0 lx | MAX | 0 dB | MAX | ... |
| TV2 | 192.168.100.5 | TELEVISION | 0x060202 | 1F LIVING ROOM | ON | 130 lx | MAX | 50 dB | MAX | ... |
| Sensor1 | 192.168.100.6 | SENSOR | 0x002A01 | 2F MAIN BEDROOM | ON | ABSENT | | | | ... |
| Sensor2 | 192.168.100.7 | SENSOR | 0x002A02 | 2F MAIN BEDROOM | ON | ABSENT | | | | ... |
| Light1 | 192.168.100.3 | LIGHTING DEVICE | 0x029001 | 2F MAIN BEDROOM | OFF | 0 lx | MAX | | | ... |
| Light2 | 192.168.100.4 | LIGHTING DEVICE | 0x029002 | 1F LIVING ROOM | ON | 310 lx | MAX | | | ... |
| ... | ... | ... | ... | ... | ... | ... | ... | ... | ... | ... |

| ROOM ID | 2F MAIN BEDROOM | 1F LIVING ROOM | 1F KITCHEN | 2F CHILD'S ROOM 1 | ··· |
|---|---|---|---|---|---|
| 2F MAIN BEDROOM | 0 dB | −10 dB | −10 dB | −5 dB | ··· |
| 1F LIVING ROOM | (−10 dB) | 0 dB | 0 dB | −10 dB | ··· |
| 1F KITCHEN | (−10 dB) | (0 dB) | 0 dB | −10 dB | ··· |
| 2F CHILD'S ROOM 1 | (−5 dB) | (−10 dB) | (−10 dB) | 0 dB | ··· |
| ··· | ··· | ··· | ··· | ··· | ··· |

| SLEEP STATE | SOUND VOLUME | ILLUMINANCE |
|---|---|---|
| NREM1 | 20 dB | 30 lx |
| NREM2 | 25 dB | 30 lx |
| NREM3 | 30 dB | 40 lx |
| NREM4 | 40 dB | 50 lx |
| REM | 20 dB | 30 lx |

| 501 | 502 | 503 | 504 | 511 | 512 | 513 | 514 | 515 | 516 | |
|---|---|---|---|---|---|---|---|---|---|---|
| DEVICE ID | IP ADDRESS | DEVICE CLASS | IDENTIFIER | PROPERTY 1 (INSTALLATION LOCATION) | PROPERTY 2 (OPERATION STATE) | PROPERTY 3 (SLEEP STATE/ ILLUMINANCE) | PROPERTY 4 (ILLUMINANCE UPPER LIMIT) | PROPERTY 5 (SOUND VOLUME) | PROPERTY 6 (SOUND VOLUME UPPER LIMIT) | ... |
| TV1 | 192.168.100.2 | TELEVISION | 0x060201 | 2F MAIN BEDROOM | ON | 40 lx | 40 lx | 30 dB | 30 dB | ... |
| TV2 | 192.168.100.5 | TELEVISION | 0x060202 | 1F LIVING ROOM | OFF | 0 lx | MAX | 0 dB | 40 dB | ... |
| Sensor1 | 192.168.100.6 | SENSOR | 0x002A01 | 2F MAIN BEDROOM | ON | NREM3 | | | | ... |
| Sensor2 | 192.168.100.7 | SENSOR | 0x002A02 | 2F MAIN BEDROOM | ON | AWAKE | | | | ... |
| Light1 | 192.168.100.3 | LIGHTING DEVICE | 0x029001 | 2F MAIN BEDROOM | ON | 40 lx | 40 lx | | | ... |
| Light2 | 192.168.100.4 | LIGHTING DEVICE | 0x029002 | 1F LIVING ROOM | OFF | 0 lx | MAX | | | ... |
| ... | ... | ... | ... | ... | ... | ... | ... | ... | ... | ... |

| DATE AND TIME (1801) | DEVICE ID (1802) | PROPERTY NUMBER (1803) | PROPERTY VALUE (1804) | ... |
|---|---|---|---|---|
| ... | ... | ... | ... | ... |
| 20150924012200 | Sensor1 | 3 | NREM3 | ... |
| 20150924012330 | TV1 | 5 | 20 | ... |
| 20150924012930 | TV1 | 5 | 30 | ... |
| 20150924012940 | Sensor1 | 3 | NREM2 | ... |
| ... | ... | ... | ... | ... |

| DEVICE ID (501) | IP ADDRESS (502) | DEVICE CLASS (503) | IDENTIFIER (504) | PROPERTY 1 (INSTALLATION LOCATION) (511) | PROPERTY 2 (OPERATION STATE) (512) | PROPERTY 3 (SLEEP STATE/ ILLUMINANCE) (513) | PROPERTY 4 (ILLUMINANCE UPPER LIMIT) (514) | PROPERTY 5 (SOUND VOLUME) (515) | PROPERTY 6 (SOUND VOLUME UPPER LIMIT) (516) | ... |
|---|---|---|---|---|---|---|---|---|---|---|
| TV1 | 192.168.100.2 | TELEVISION | 0x060201 | 2F MAIN BEDROOM | ON | 30 lx | 30 lx | 25 dB | 25 dB | ... |
| TV2 | 192.168.100.5 | TELEVISION | 0x060202 | 1F LIVING ROOM | OFF | 0 lx | MAX | 0 dB | 35 dB | ... |
| Sensor1 | 192.168.100.6 | SENSOR | 0x002A01 | 2F MAIN BEDROOM | ON | NREM2 | | | | ... |
| Sensor2 | 192.168.100.7 | SENSOR | 0x002A02 | 2F MAIN BEDROOM | ON | AWAKE | | | | ... |
| Light1 | 192.168.100.3 | LIGHTING DEVICE | 0x029001 | 2F MAIN BEDROOM | ON | 30 lx | 30 lx | | | ... |
| Light2 | 192.168.100.4 | LIGHTING DEVICE | 0x029002 | 1F LIVING ROOM | OFF | 0 lx | MAX | | | ... |
| ... | ... | ... | ... | ... | ... | ... | ... | ... | ... | ... |

| ROOM ID | 2F MAIN BEDROOM | 1F LIVING ROOM | 1F KITCHEN | 2F CHILD'S ROOM 1 | ••• |
|---|---|---|---|---|---|
| 2F MAIN BEDROOM | +1 dB | −10 dB | −10 dB | −5 dB | ••• |
| 1F LIVING ROOM | (−10 dB) | 0 dB | 0 dB | −10 dB | ••• |
| 1F KITCHEN | (−10 dB) | (0 dB) | 0 dB | −10 dB | ••• |
| 2F CHILD'S ROOM 1 | (−5 dB) | (−10 dB) | (−10 dB) | 0 dB | ••• |
| ••• | ••• | ••• | ••• | ••• | ••• |

| DEVICE ID (501) | IP ADDRESS (502) | DEVICE CLASS (503) | IDENTIFIER (504) | PROPERTY 1 (INSTALLATION LOCATION) (511) | PROPERTY 2 (OPERATION STATE) (512) | PROPERTY 3 (SLEEP STATE/ ILLUMINANCE) (513) | PROPERTY 4 (ILLUMINANCE UPPER LIMIT) (514) | PROPERTY 5 (SOUND VOLUME) (515) | PROPERTY 6 (SOUND VOLUME UPPER LIMIT) (516) | ... |
|---|---|---|---|---|---|---|---|---|---|---|
| TV1 | 192.168.100.2 | TELEVISION | 0x060201 | 2F MAIN BEDROOM | ON | 30 lx | 30 lx | 24 dB | 24 dB | ... |
| TV2 | 192.168.100.5 | TELEVISION | 0x060202 | 1F LIVING ROOM | OFF | 0 lx | MAX | 0 dB | 35 dB | ... |
| Sensor1 | 192.168.100.6 | SENSOR | 0x002A01 | 2F MAIN BEDROOM | ON | NREM2 | | | | ... |
| Sensor2 | 192.168.100.7 | SENSOR | 0x002A02 | 2F MAIN BEDROOM | ON | AWAKE | | | | ... |
| Light1 | 192.168.100.3 | LIGHTING DEVICE | 0x029001 | 2F MAIN BEDROOM | ON | 30 lx | 30 lx | | | ... |
| Light2 | 192.168.100.4 | LIGHTING DEVICE | 0x029002 | 1F LIVING ROOM | OFF | 0 lx | MAX | | | ... |
| ... | ... | ... | ... | ... | ... | ... | ... | ... | ... | ... |

CONTROL METHOD, CONTROLLER, AND DEVICE

BACKGROUND

1. Technical Field

The present disclosure relates to control methods, controllers, and devices which limit operation of a device for use by a non-sleeper in accordance with a sleeper's state.

2. Description of the Related Art

A certain number of people think that a couple desirably sleep in the same bedroom for use by the couple in view of communications and caring. However, there is a problem that household sound generated by one person in a couple may interfere with sleep of the other due to a difference in life rhythm.

For example, when one is sleeping while the other desires to enjoy music by using an audio device or the like for relaxation before sleeping, sleeper's sleep may be interrupted.

Japanese Unexamined Patent Application Publication No. 2015-15159 discloses a bedroom environment generation system including shielding blinds, a directional loudspeaker, and range-selective illuminating means capable of selectively irradiating illumination light only to any one person and allowing video and music enjoyment in consideration of a sleeper.

SUMMARY

However, the related art described above requires further improvements.

In one general aspect, the techniques disclosed here feature a method of controlling a device located in a predetermined space, the method including: obtaining sleep information of a person present in a first space from a biological sensor disposed in the first space, the sleep information indicating a sleep state of the person and the first space includes a first device; determining, by a processor, a first sound volume to be set for the first device based on the obtained sleep information and a first database indicating a correspondence between the sleep state and a target sound volume of a corresponding device, the target sound volume of the corresponding device being a predetermined sound volume which does not awake a sleeping person at the sleep state and still be heard by an awake person; and transmitting, to the first device, a first command for setting the first sound volume in the first device as a sound volume upper-limit value.

These general and specific aspects may be implemented using a system, a method, and a computer program, and any combination of systems, methods, and computer programs.

According to the present disclosure, a device can be used by a non-sleeper without awaking a sleeper.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram of an example of device management information in a device database;

FIG. 6 is a diagram of an example of soundproof performance information in a room database;

FIG. 7 is a diagram of an example of limitation information stored in a storage unit;

FIG. 9 is a diagram of an example of updated device management information in the device database;

FIG. 18 is a diagram of an example of log information in a log database;

FIG. 19 is a diagram of device management information when soundproof performance information is not corrected;

FIG. 20 is a diagram of corrected soundproof performance information in a room database;

FIG. 21 is a diagram of device management information when the soundproof performance information is corrected;

Figure 1:
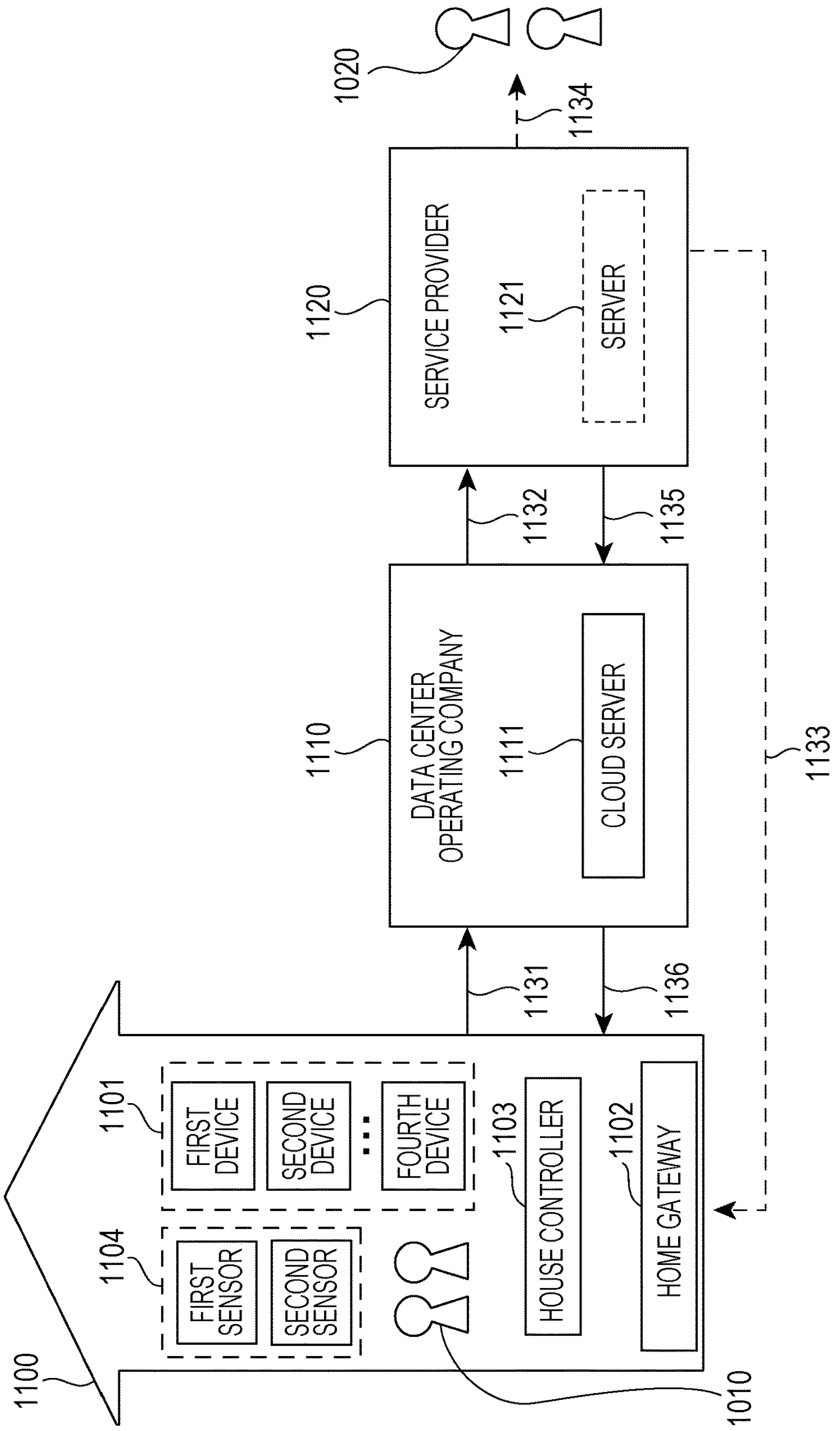
FIG. 1 is a diagram of an overview of service to be provided by a device control system in the present embodiments.

DETAILED DESCRIPTION (Underlying Knowledge Forming Basis of the Present Disclosure)

In studies of human sleep, influences on sleep by heat, sound, and light environment before and during sleeping have been revealed, and air conditioner control, lighting device control, and so forth suitable for sleep have been considered.

On the other hand, in consideration of a house where a plurality of persons in a family are living, each life rhythm is different, and it is rare that all persons simultaneously go to bed and get out of bed. Therefore, household noise of a non-sleeper may interfere with sleeper's sleep. Thus, the non-sleeper cares about the sleeper, and tries to act so as not to make household noise as little as possible. However, it is difficult to determine the sleeper's state, and the non-sleeper may restrict his or her activity more than required. Thus, there is a need to easily know the sleeper's state to act as freely as possible. In Japanese Unexamined Patent Application Publication No. 2015-15159, technical solutions for satisfying this need are not sufficiently studied.

From the above considerations, the inventor has conceived disclosures of aspects according to the present disclosure as follows.

(1) A first aspect of the present disclosure is directed to a method of controlling a device located in a predetermined space, the method including: obtaining sleep information of a person present in a first space from a biological sensor disposed in the first space, the sleep information indicating a sleep state of the person and the first space includes a first device; determining, by a processor, a first sound volume to be set for the first device based on the obtained sleep information and a first database indicating a correspondence between the sleep state and a target sound volume of a corresponding device, the target sound volume of the corresponding device being a predetermined sound volume which does not awake a sleeping person at the sleep state and still be heard by an awake person; and transmitting, to the first device, a first command for setting the first sound volume in the first device as a sound volume upper-limit value.

According to this aspect, the upper-limit value of the sound to be outputted from the device is set at a value which allows sleeper's sleep to be kept and allows the use of the device by a non-sleeper to be continued. Therefore, the non-sleeper can use the device without concern for the sleep state of the sleeper. Also, it is possible to prevent sleeper's sleep from being interrupted.

(2) In the first aspect, the first database may further indicate a correspondence between the sleep state and a target illuminance level of the corresponding device, and the method may further including: determining, by the processor, a first illuminance level of the first device based on the obtained sleep information and the first database, and transmitting, to the first device, a second command for setting the first illuminance level in the first device as an illuminance upper-limit value, the target illuminance level of the corresponding device being a predetermined illuminance level which does not awake the sleeping person at the sleep state while providing visibility for the awake person.

According to this aspect, the upper-limit value of lighting of the device is set at a value which allows sleeper's sleep to be kept and allows the use of the device by a non-sleeper to be continued. Therefore, the non-sleeper can use the device without concern for the sleep state of the sleeper. Also, it is possible to prevent sleeper's sleep from being interrupted.

(3) In the first aspect, the method may further include: determining, by the processor, a second sound volume of a second device located in a second space based on the obtained sleep information, the first database, and a second database indicating a reduction amount of sound when the sound is transmitted from the second space to the first space, the second sound volume being smaller than the first sound volume; and transmitting, to the second device, a third command for setting the second sound volume in the second device as a sound volume upper-limit value.

According to this aspect, it is possible to decide, as an upper-limit value of the sound volume of the device, a value in accordance with soundproof performance between a room where the device is installed and a room where a sleeper is present.

(4) In the first aspect, the biological sensor may be attached to the person.

(5) In the first aspect, the first space may include a bedroom.

(6) In the first aspect, the biological sensor may include a vibration sensor installed in a bedding disposed in the bedroom.

(7) In the first aspect, the biological sensor may include a radio sensor inside a bedding disposed in the bedroom or installed in a predetermined range from the bedding.

(8) In the first aspect, the biological sensor may measure a body motion, a respiration rate, and a heart rate of the person, and the sleep information may be calculated based on a number of times the person turns-over per unit time calculated from the body motion, the respiration rate of the person, and the heart rate of the person.

(9) In the first aspect, the method further include: storing sleep log information in a memory, the sleep log information indicating a correspondence between the sleep state and a corresponding date, storing operation log information in the memory, the operation log information indicating a correspondence between a history of changing a sound volume of the first device and a corresponding date, determining, by the processor, based on the sleep log information and the operation log information, whether the sleep state indicated in the sleep information becomes shallow after increasing the sound volume of the first device, and correcting the first database when it is determined by the processor that the sleep state indicated in the sleep information becomes shallow a predetermined number of times or more after the increasing the sound volume of the first device.

According to this aspect, it is possible to prevent sleeper's sleep from becoming shallow when the sound volume of the device is changed.

(10) In the first aspect, the method may further include: storing sleep log information in a memory, the sleep log information indicating a correspondence between the sleep state and a corresponding date; storing operation log information in the memory, the operation log information indicating a correspondence between a history of increasing a sound volume of the second device and a corresponding date; determining, based on the sleep log information and the operation log information, whether the sleep state indicated in the sleep information becomes shallow after increasing the sound volume of the second device; and correcting the second database when it is determined by the processor that the sleep state indicated in the sleep information becomes shallow a predetermined number of times or more after the increasing the sound volume of the second device.

According to this aspect, it is possible to prevent sleeper's sleep from becoming shallow when the sound volume of the device is changed.

(11) A second aspect of the present disclosure is directed to a method of controlling a device included in a predetermined space, the method including: receiving, from a processor, a first command for setting a first sound volume in the device as a sound volume upper-limit value; and setting, by the processor, the first sound volume as the sound volume upper-limit value in the device, wherein the first sound volume is determined by the processor based on a database and sleep information of a person present in the predetermined space, the sleep information being obtained from a biological sensor disposed in the predetermined space, the sleep information indicates a sleep state of the person, the database indicates a correspondence between the sleep state and a target sound volume of a corresponding device, and the target sound volume of the corresponding device is a predetermined sound volume which does not awake a sleeping person at the sleep state and still be heard by an awake person.

According to this aspect, the upper-limit value of the sound to be outputted from the device is set at a value which allows sleeper's sleep to be kept and allows the use of the device by a non-sleeper to be continued. Therefore, the non-sleeper can use the device without concern for the sleep state of the sleeper. Also, it is possible to prevent sleeper's sleep from being interrupted.

(12) In the second aspect, the method may further include: receiving, from the processor, a second command for setting a first illuminance level in the device as an illuminance upper-limit value; and setting the first illuminance level in the device as the illuminance upper-limit value, wherein the database may further indicate a correspondence between the sleep state and a target illuminance level of a corresponding device, the first sound volume may be determined by the processor based on the sleep information and the database, and the target illuminance level of the corresponding device may be a predetermined illuminance level which does not awake the sleeping person at the sleep state while providing visibility for the awake person.

According to this aspect, the upper-limit value of lighting of the device is set at a value which allows sleeper's sleep to be kept and allows the use of the device by a non-sleeper to be continued. Therefore, the non-sleeper can use the device without concern for the sleep state of the sleeper. Also, it is possible to prevent sleeper's sleep from being interrupted.

(13) In the second aspect, the method may further include: determining, by the processor, whether a second sound volume, which is a current sound volume of the device, exceeds the first sound volume; and causing the device to output sound at the first sound volume when it is determined that the second sound volume exceeds the first sound volume.

According to this aspect, when the sound volume outputted from the device exceeds the upper-limit value, the sound volume is changed to the upper-limit value. Therefore, it is possible to prevent sleeper's sleep from being interrupted.

(14) In the second aspect, the method may further include changing a sound volume of the device from the second sound volume to the first sound volume at a predetermined rate of change in a stepwise manner.

According to this aspect, the sound volume outputted from the device is mildly decreased to be changed to the upper-limit value. Therefore, it is possible to prevent sleeper's sleep from being interrupted.

(15) In the second aspect, the method may further include changing a sound volume of the device to the first sound volume or lower at a predetermined rate of change in a stepwise manner.

According to this aspect, the sound volume outputted from the device is mildly decreased to be changed to the upper-limit value. Therefore, it is possible to prevent sleeper's sleep from being interrupted.

(16) In the second aspect, the method may further include: determining, by the processor, whether a second sound volume, which is a current sound volume of the device, exceeds the first sound volume; and when it is determined that the second sound volume exceeds the first sound volume and the device can replay contents including video and sound with subtitles, causing the device to replay the contents at the first sound volume with the subtitles.

According to this aspect, even if the sound volume outputted from the device is decreased to the upper-limit value (first sound volume), a decrease in sound volume can be compensated with subtitles.

(17) In the second aspect, the device may include a display, and the method may further include: determining whether a second sound volume, which is a current sound volume of the device, exceeds the first sound volume; and causing a notification prompting for decreasing a sound volume of the device in a stepwise manner to be displayed on the display when it is determined that the second sound volume exceeds the first sound volume.

According to this aspect, it is possible to cause the non-sleeper to mildly decrease the sound volume of the device, thereby preventing sleeper's sleep from being interrupted.

In the following, embodiments of the present disclosure are described with reference to the drawing. Note that the embodiments described below are each merely a specific example of the present disclosure. Numerical values, shapes, components, steps, and a sequence of the steps in the embodiments described below are merely examples, and are not intended to restrict the present disclosure. Also, among the components in the following embodiments, those not described in independent claims representing a highest-order concept are described as any components. Also, details in all of the embodiments can be combined in any manner.

(Overview of Service to Be Provided)

First, the overview of service to be provided by the device control system in the present embodiments is described.

FIG. 1 is a diagram of an overview of service to be provided by a device control system in the embodiments. The device control system includes a group 1100, a data center operating company 1110, and a service provider 1120.

The group 1100 is a home such as, for example, a separate house or multiple dwelling house, irrespectively of the size. The group 1100 includes a plurality of devices 1101 including first to fourth devices, a plurality of sensors 1104 including first and second sensors, a house controller 1103, and a home gateway 1102. The plurality of devices 1101 include a device connectable to the Internet (such as, for example, smartphone, personal computer (PC), television, or stereo) and a device unconnectable to the Internet by itself (such as, for example, lighting device, washing machine, or refrigerator). The plurality of devices 1101 may include a device connectable to the Internet via the home gateway 1102 although unconnectable to the Internet by itself. Also, a user 1010 uses the plurality of devices 1101 in the group 1100.

The data center operating company 1110 includes a cloud server 1111. The cloud server 1111 is a virtual server in cooperation with various devices via the Internet. The cloud server 1111 mainly manages, for example, enormous data (big data) that is difficult to handle by a normal database management tool or the like. The data center operating company 1110 performs management of data, management of the cloud server 1111, operation of a data center which performs these managements, and so forth. Details of service performed by the data center operating company 1110 will be described further below.

Figure 2:
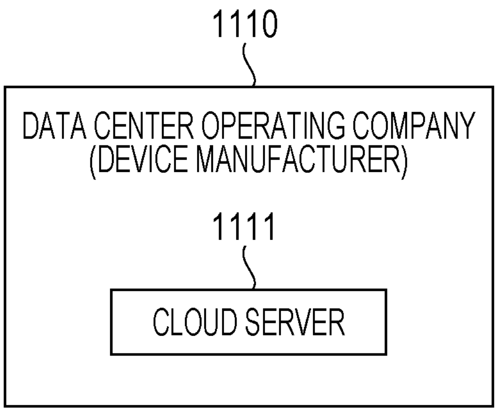
FIG. 2 is a diagram of an example in which a device manufacturer corresponds to a data center operating company in the present embodiments.
Figure 3:
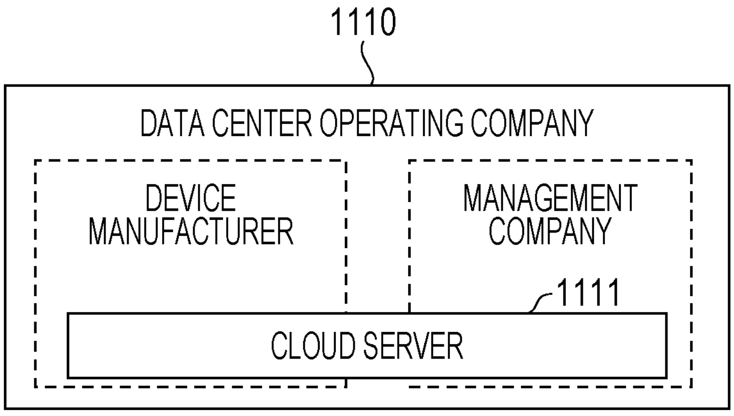
FIG. 3 is a diagram of an example in which either one or both of the device manufacturer and a management company correspond to the data center operating company in the present embodiments.

Here, the data center operating company 1110 is not limited to a company which only performs management of data and management of the cloud server 1111. For example, as depicted in FIG. 2, when a device manufacturer which develops or manufactures one of the plurality of devices 1101 performs management of data, management of the cloud server 1111, or the like, that device manufacturer corresponds to the data center operating company 1110. Also, the data center operating company 1110 is not limited to a single company. For example, as depicted in FIG. 3, when a device manufacturer and a management company perform management of data or management of the cloud server 1111 in coordination with each other or in a distributed manner, either one or both correspond to the data center operating company 1110.

The service provider 1120 includes a server 1121. The server 1121 herein is irrespective of the size, and also includes, for example, a memory in a personal PC. Also, the service provider 1120 may not include the server 1121.

Next, a flow of information in the above-described device control system is described.

First, the first to fourth devices, the first and second sensor, and the house controller 1103 of the group 1100 each transmit log information to the cloud server 1111 of the data center operating company 1110. The cloud server 1111 accumulates the log information of the first to fourth devices, sensor information of the first and second sensors, and logs of the house controller 1103 (an arrow 1131 in FIG. 1).

Here, the log information is information indicating, for example, operation details, operating statuses, operation date and time, and so forth of the plurality of devices 1101. For example, the log information includes sound volume operation history and viewing history of a television, video recording timer information of a recorder, operation date and time and amount of laundry of a washing machine, operation history of a lighting device, open/close date and time of a refrigerator, the number of times of opening and closing the refrigerator, and so forth. However, the log information is not restricted to these, and may include various information obtainable from various devices.

Note that the log information may be provided directly from the plurality of devices 1101 themselves via the Internet to the cloud server 1111. Also, the log information may be once accumulated in the house controller 1103 or the home gateway 1102 from the plurality of the devices 1101 and then provided from the house controller 1103 or the home gateway 1102 to the cloud server 1111. Furthermore, sensor data of the plurality of sensors 1104 as log information may also be provided to the cloud server 1111.

Next, the cloud server 1111 of the data center operating company 1110 provides the accumulated log information to the service provider 1120 in a certain unit. Here, the certain unit may be a unit that can be provided to the service provider 1120 by sorting out the information accumulated by the data center operating company 1110 or a unit requested by the service provider 1120. Also, while it is described that the information is provided in the certain unit, the information may be provided not in the certain unit, and the information amount to be provided may be changed in accordance with the situation. The log information is stored as necessary in the server 1121 owned by the service provider 1120 (an arrow 1132 in FIG. 1).

Then, the service provider 1120 sorts out the log information into information suitable for the service to be provided to the user, and provides the information to the user or the house controller 1103. The user to whom the information is provided may be the user 1010 who uses the plurality of devices 1101 or an external user 1020.

As a method of providing the information to the users 1010 and 1020, for example, the information may be provided directly to the user 1020 from the service provider 1120 (arrows 1133 and 1134 in FIG. 1). Also, as a method of providing the information to the user 1010, for example, the information may be provided to the user 1010 via the cloud server 1111 of the data center operating company 1110 again (arrows 1135 and 1136 in FIG. 1). Furthermore, the cloud server 1111 of the data center operating company 1110 may sort out the log information into information suitable for the service to be provided to the user and provide the information to the service provider 1120.

Note that the user 1010 may be different from or identical to the user 1020.

First Embodiment

In a first embodiment, an example is described in which a device which generates at least one of light and sound is used as the device 1101, for example, a television receiver (hereinafter simply referred to as a "television"), a lighting device, or the like.

(Structure)

Figure 4:
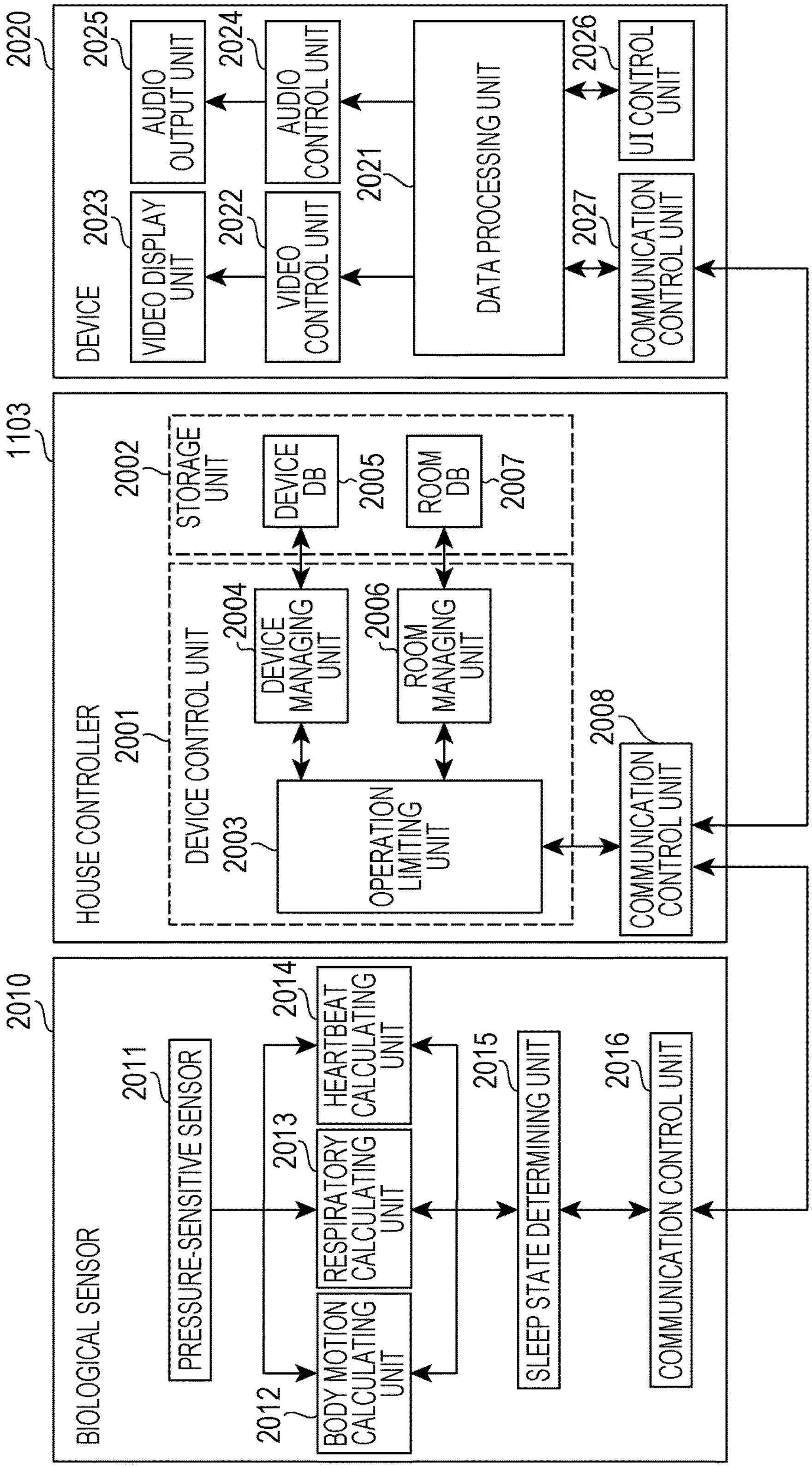
FIG. 4 is a diagram of structure of a device control system according to a first embodiment.

FIG. 4 is a block diagram schematically depicting the structure of a device control system according to the first embodiment of the present disclosure. As depicted in FIG. 4, the device control system in the first embodiment includes a biological sensor 2010, a device 2020, and the house controller 1103.

The biological sensor 2010 includes a pressure-sensitive sensor 2011, a body motion calculating unit 2012, a respiratory calculating unit 2013, a heartbeat calculating unit 2014, a sleep state determining unit 2015, and a communication control unit 2016. The body motion calculating unit 2012, the respiratory calculating unit 2013, the heartbeat calculating unit 2014, and the sleep state determining unit 2015 each include, for example, a central processing unit (CPU) and a memory. The body motion calculating unit 2012, the respiratory calculating unit 2013, the heartbeat calculating unit 2014, and the sleep state determining unit 2015 may not be restricted to include a CPU, but may include other hardware which carries out the same function.

The pressure-sensitive sensor 2011 is disposed in contact with, for example, bedding. The pressure-sensitive sensor 2011 detects fine vibrations of a person (sleeper). The pressure-sensitive sensor 2011 outputs the detection result to the body motion calculating unit 2012, the respiratory calculating unit 2013, and the heartbeat calculating unit 2014.

Fine vibrations of the sleeper detected by the pressure-sensitive sensor 2011 include vibrations due to body motion (for example, turning over during sleeping) of the sleeper, vibrations due to respiration of the sleeper, and vibrations due to heartbeats of the sleeper, each having different cycles.

The body motion calculating unit 2012 extracts vibrations in a cycle corresponding to body motion (for example, turning over during sleeping) of the sleeper from the fine vibrations of the sleeper detected by the pressure-sensitive sensor 2011, and calculates a body motion state (for example, a turning-over count per minute) of the sleeper.

The respiratory calculating unit 2013 extracts vibrations in a cycle corresponding to respiration of the sleeper from the fine vibrations of the sleeper detected by the pressure-sensitive sensor 2011, and calculates a respiration rate of the sleeper per minute.

The heartbeat calculating unit 2014 extracts vibrations in a cycle corresponding to heartbeat of the sleeper from the fine vibrations of the sleeper detected by the pressure-sensitive sensor 2011, and calculates a heart rate of the sleeper per minute.

The sleep state determining unit 2015 determines a sleep state of the sleeper based on the calculation results of the body motion calculating unit 2012, the respiratory calculating unit 2013, and the heartbeat calculating unit 2014. As a sleep state of the sleeper, the sleep state determining unit 2015 determines, for example, an absent state, an awake state, a REM sleeping (REM) state, a non-REM sleep stage 1 (NREM1) state, a non-REM sleep stage 2 (NREM2) state, a non-REM sleep stage 3 (NREM3) state, and a non-REM sleep stage 4 (NREM4) state, in the present embodiment. The sleep state determining unit 2015 notifies the house controller 1103 of the sleep state of the sleeper via the communication control unit 2016.

The device 2020 is included in the device 1101 (FIG. 1). The device 2020 is, for example, a television in the present embodiment. The device 2020 includes a data processing unit 2021, a video control unit 2022, a video display unit 2023, an audio control unit 2024, an audio output unit 2025, a user interface (UI) control unit 2026, and a communication control unit 2027. The data processing unit 2021, the video control unit 2022, and the audio control unit 2024 each include, for example, a CPU and a memory. The data processing unit 2021, the video control unit 2022, and the audio control unit 2024 may not be restricted to include a CPU, but may include other hardware which carries out the same function.

The data processing unit 2021 processes, for example, a television multicast signal obtained via an antenna, and extracts a video signal and an audio signal. The data processing unit 2021 outputs the extracted video signal to the video control unit 2022, and outputs the extracted audio signal to the audio control unit 2024. Also, the data processing unit 2021 communicates with the house controller 1103 via the communication control unit 2027. The video control unit 2022 uses the video signal inputted from the data processing unit 2021 to cause video to be displayed on the video display unit 2023. The video display unit 2023 includes, for example, a liquid-crystal display panel.

The UI control unit 2026 includes a sound volume button to be operated by the user. The UI control unit 2026 accepts operation of the sound volume button by the user and outputs an operation amount to the data processing unit 2021. The data processing unit 2021 outputs the operation amount of the sound volume button inputted from the UI control unit 2026 to the audio control unit 2024. The audio control unit 2024 uses an audio signal inputted from the data processing unit 2021 and the operation amount of the sound volume button to output audio from the audio output unit 2025. The audio output unit 2025 includes, for example, a loudspeaker.

Note that the device 2020 is not restricted to the television. The device 2020 may be, for example, a smartphone, personal computer (PC), tablet, or the like which generates video (light) and sound, or may be a stereo which generates sound only. For example, in the case of a device not accompanied by video outputs, such as a stereo, the device 2020 may not include the video display unit 2023 and the video control unit 2022. Furthermore, the device 2020 may be, for example, a lighting device which generates only light. For example, in the case of a lighting device, the device 2020 may include an electric lamp and a lighting control unit which controls a light amount of the electric lamp, in place of the data processing unit 2021, the video control unit 2022, the video display unit 2023, the audio control unit 2024, and the audio output unit 2025.

While only one device 2020 as a television is depicted in FIG. 4, as will be described further below, the device control system of the first embodiment includes a plurality of devices 2020 such as a television, lighting device, and so forth.

The house controller 1103 controls operation of the devices 2020 connected to the same network. The house controller 1103 includes a device control unit 2001, a storage unit 2002, and a communication control unit 2008. The device control unit 2001 includes an operation limiting unit 2003, a device managing unit 2004, and a room managing unit 2006. The device control unit 2001 includes, for example, a CPU and a memory. The device control unit 2001 may not be restricted to include a CPU, but may include other hardware which carries out the same function. The storage unit 2002 includes a device database (DB) 2005 and a room DB 2007. The storage unit 2002 is configured of a non-volatile memory, for example, a hard disk drive, flash memory, or the like.

The device managing unit 2004 manages device management information 500 (FIG. 5, which will be described further below) stored in the device DB 2005. The room managing unit 2006 manages soundproof performance information 600 (FIG. 6, which will be described further below) indicating soundproof performance between rooms stored in the room DB 2007.

FIG. 5 is a diagram of an example of the device management information 500 stored in the device DB 2005. The device managing unit 2004 of the house controller 1103 uses the device management information 500 to manage the devices including the device 2020 and the biological sensor 2010. The device managing unit 2004 uses information transmitted from the devices 2020, the biological sensor 2010, and so forth to generate the device management information 500. The device managing unit 2004 stores the generated device management information 500 in the device DB 2005. The device management information 500 includes a device ID 501, an IP address 502, a device class 503, an identifier 504, and properties 511 to 516.

The device ID 501 is a unique identifier which specifies any of the devices including in the devices 2020 and the biological sensor 2010. The IP address 502 indicates an address of a device when the house controller 1103 accesses the device on the network. The device class 503 indicates a name of a device. In FIG. 5, two "televisions", two "biological sensors", and two "lighting devices" are depicted as the device class 503. The identifier 504 is a unique code provided to a device.

The property 511 indicates an installation location of a device. The property 512 indicates an operation state (ON or OFF) of a device. The property 513 indicates a current sleep state or illuminance. The property 514 indicates an illuminance upper limit being set. The property 515 indicates a current sound volume. The property 516 indicates a sound volume upper limit being set.

The house controller 1103 manages devices including the devices 2020 such as a television and lighting device and the biological sensor 2010 as abstraction objects. In the abstraction object of each device, control information and so forth are managed as properties. In this manner, the device management information 500 is managed in units of property. Thus, each of the properties 511 to 516 has a different meaning for each device class 503.

For example, when the device class 503 is "sensor", the property 513 indicates a sleep state of a sensor's detection target (sleeper) (that is, the determination result of the sleep state determining unit 2015 of the biological sensor 2010). On the other hand, when the device class 503 is "television" or "lighting device", the property 513 indicates illuminance. For example, when the device class 503 is "television" or "lighting device", the property 514 indicates illuminance. When the device class 503 is "sensor", the property 514 does not contain information. For example, when the device class 503 is "television", the properties 515 and 516 each indicate a sound volume. On the other hand, when the device class 503 is "sensor" or "lighting device", the properties 515 and 516 do not contain information.

The state indicated by the device management information 500 of FIG. 5 is described. The television and the lighting device with the property 511 (installation location) being "1F living room" are "ON". Therefore, it can be thought that the television is viewed in the living room on the first floor.

On the other hand, since the property 513 (sleep state) of each of the device IDs 501 being "Sensor1" and "Sensor2" indicates "absent", it can be found that no sleeper is present. Thus, the property 514 (illuminance upper limit) and the property 516 (sound volume upper limit) are all set as "MAX". That is, in the device management information 500 of FIG. 5, no sleeper is present, and therefore neither illuminance nor sound volume is limited.

FIG. 6 is a diagram of an example of the soundproof performance information 600 stored in the room DB 2007. The soundproof performance information 600 indicates soundproof performance between rooms. In the soundproof performance information 600, room IDs 601 are arranged in a row direction and a column direction, and soundproof performance values 602 between rooms are arrayed in a matrix.

In the soundproof performance information 600 of FIG. 6, the soundproof performance value 602 between the same rooms is set at "0 dB". This means that no soundproof performance can be achieved between the same rooms. In FIG. 6, the soundproof performance value 602 between "2F main bedroom" and "1F living room" is set at "−10 dB". This "−10 dB" means that the sound volume of the device 2020 of "1F living room" is decreased by 10 dB to reach "2F main bedroom".

An initial value of the soundproof performance value 602 in the soundproof performance information 600 may be manually inputted by the user. The input of the soundproof performance value 602 by the user may be in a questionnaire form. The room managing unit 2006 uses the input result by the user to generate soundproof performance information 600 in a tabular form depicted in FIG. 6.

FIG. 7 is a diagram of an example of limitation information 700 stored in the storage unit 2002. The limitation information 700 includes a sleep state 701, a sound volume limitation value 702, and an illuminance limitation value 703. The sound volume limitation value 702 and the illuminance limitation value 703 are set in advance so as to correspond to the sleep state 701.

As depicted in FIG. 7, as a sleep state 701, the limitation information 700 includes a sleep state NREM1, a sleep state NREM2, a sleep state NREM3, and a sleep state NREM4. Human sleep in the sleep state NREM1 is the shallowest, human sleep gets deeper as the state becomes the sleep state NREM2 and then the sleep state NREM3, and human sleep in the sleep state NREM4 is the deepest.

In FIG. 7, the sound volume limitation value is set at 20 dB and the illuminance limitation value is set at 30 lx so as to correspond to the sleep state NREM1; the sound volume limitation value is set at 25 dB and the illuminance limitation value is set at 30 lx so as to correspond to the sleep state NREM2; the sound volume limitation value is set at 30 dB and the illuminance limitation value is set at 40 lx so as to correspond to the sleep state NREM3; and the sound volume limitation value is set at 40 dB and the illuminance limitation value is set at 50 lx so as to correspond to the sleep state NREM4. In this manner, as sleep gets deeper, the sound volume and illuminance limitation values are higher.

Also, the sound volume limitation value is set at 20 dB and the illuminance limitation value is set at 30 lx so as to correspond to a sleep state REM. Note that the sound volume and illuminance limitation values depicted in FIG. 7 are merely examples. In the first embodiment, the sound volume and illuminance limitation values are not restricted to the numerical values depicted in FIG. 7, and other numerical values may be used.

Referring back to FIG. 4, the operation limiting unit 2003 of the device control unit 2001 uses the device management information 500, the soundproof performance information 600, and the limitation information 700 to set sound volume and illuminance (light amount) upper-limit values of the device 2020 each at a first value via the communication control unit 2008. Functions of the operation limiting unit 2003 will be described in detail further below.

Note that while biological sensor 2010 of FIG. 4 includes the pressure-sensitive sensor 2011 disposed in contact with, for example, bedding, the structure of the biological sensor 2010 in the present embodiment is not restricted to the one depicted in FIG. 4.

Figure 8:
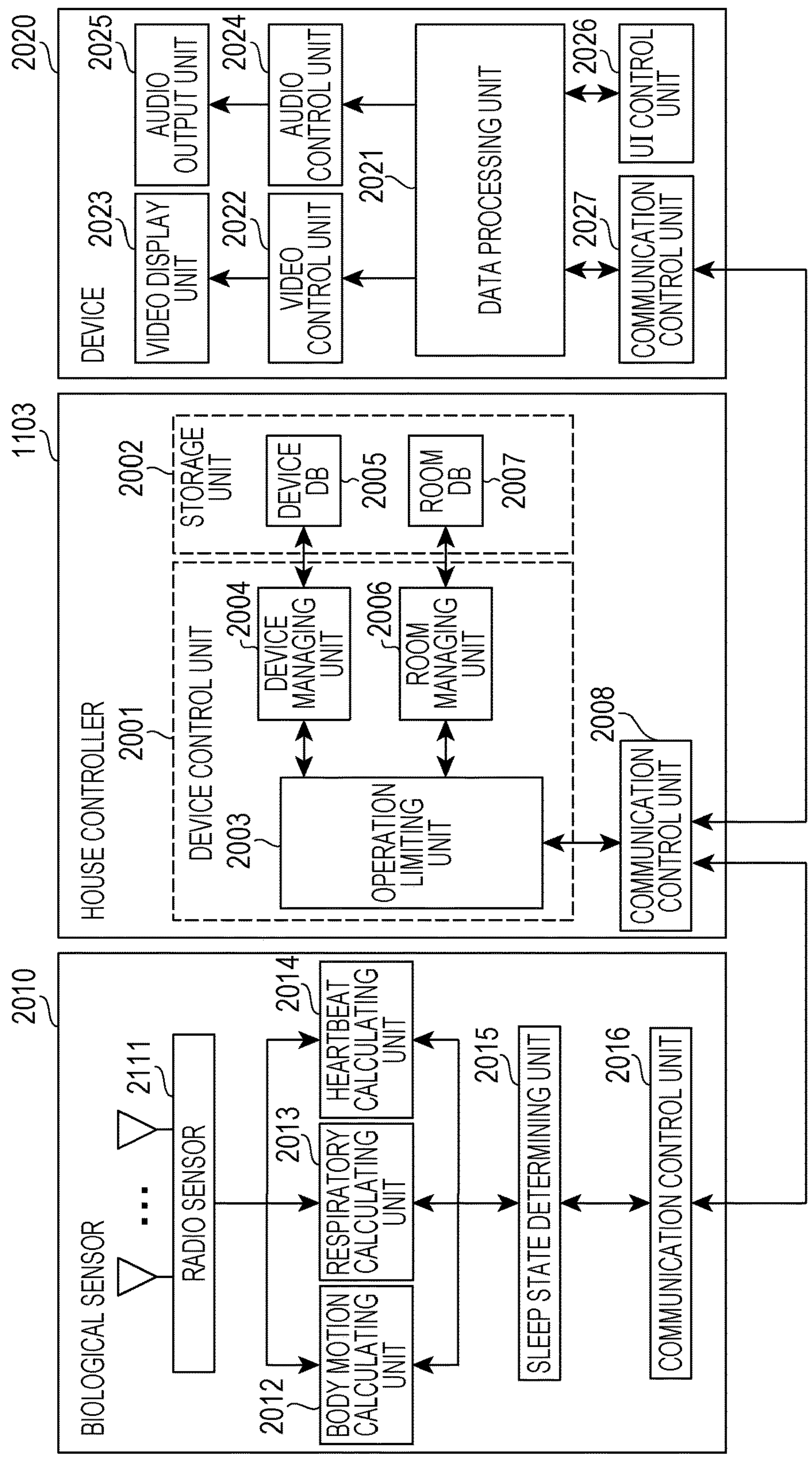
FIG. 8 is a diagram of structure of the device control system using a radio sensor in the first embodiment.

FIG. 8 is a block diagram schematically depicting the structure of the device control system including the biological sensor 2010 in a structure different from that of FIG. 4. The biological sensor 2010 of FIG. 8 includes a radio sensor 2111 in place of a pressure-sensitive sensor.

The radio sensor 2111 transmits an electromagnetic wave of, for example, a 24 GHz band, and receives the electromagnetic wave reflected on a person (sleeper) to detect fine vibrations (body motion of the sleeper). The radio sensor 2111 may be installed in, for example, bedding. Note that the radio sensor 2111 may be installed at a location away from bedding, such as a ceiling.

Furthermore, in place of a pressure-sensitive sensor or radio sensor, another sensor may be used. For example, an acceleration sensor may be used to detect movement of the sleeper. Alternatively, for example, a sensor with liquid enclosed therein to detect vibrations of the sleeper based on liquid fluctuation may be used. In short, any sensor may be used as long as the sensor can detect body motion of the sleeper as a vibration sensor. Note that the vibration sensor may be attached to the person (sleeper).

Note that while the biological sensor 2010 includes the body motion calculating unit 2012, the respiratory calculating unit 2013, the heartbeat calculating unit 2014, and the sleep state determining unit 2015 and a sleep state is determined by the biological sensor 2010 and then the determination result is transmitted from the biological sensor 2010 to the house controller 1103 in the device control systems of FIG. 4 and FIG. 8, the present embodiment is not restricted to this structure.

For example, the house controller 1103 may include the body motion calculating unit 2012, the respiratory calculating unit 2013, the heartbeat calculating unit 2014, and the sleep state determining unit 2015. In this structure, the biological sensor 2010 transmits detection data of the pressure-sensitive sensor 2011 or the radio sensor 2111 to the house controller 1103 via the communication control unit 2016. The house controller 1103 uses the detection data transmitted from the biological sensor 2010 to determine a sleep state.

Next, with reference to FIG. 9, the functions of the operation limiting unit 2003 of the device control unit 2001 in the house controller 1103 are described. In the device management information 500 of FIG. 5, since no sleeper is present, neither illuminance nor sound volume is limited. By contrast, in the first embodiment, if a sleeper is present, the operation limiting unit 2003 limits the illuminance and sound volume upper-limit values of the device 2020.

FIG. 9 is a diagram of an example of the device management information 500 when both of a sleeper and a non-sleeper are present, which is different from the device management information 500 of FIG. 5. In the properties 513 to 516 in the device management information 500 of FIG. 9, values changed from those in the device management information 500 of FIG. 5 are underlined (except those turned OFF).

In the device management information 500 of FIG. 9, in each device with the property 511 (installation location) being "2F main bedroom", the property 513 (sleep state) with the device ID 501 being "Sensor1" indicates "NREM3", and the property 513 (sleep state) with the device ID 501 being "Sensor2" indicates "awake". Therefore, it is indicated that, of two persons in "2F main bedroom", one is a sleeper and the other is a non-sleeper.

Also, the property 512 (operation state) of each of the television and the lighting device with the property 511 (installation location) being "2F main bedroom" indicates "ON". Therefore, it is indicated that, of two persons in "2F main bedroom", the non-sleeper is viewing television.

Thus, the operation limiting unit 2003 reads the limitation information 700 (FIG. 7) stored in the storage unit 2002, and extracts "30 dB" as the sound volume limitation value 702 and "40 lx" as the illuminance limitation value 703 corresponding to the sleep state 701 being "NREM3".

Also, the operation limiting unit 2003 reads the soundproof performance information 600 (FIG. 6) stored in the room DB 2007, and extracts "0 dB" as the soundproof performance value 602 of "2F main bedroom" and "10 dB" as the soundproof performance value 602 of "1F living room" corresponding to the room ID 601 being "2F main bedroom".

The operation limiting unit 2003 sets the illuminance limitation value 703 (FIG. 7) in the limitation information 700 as an illuminance upper limit (property 514 of FIG. 9) of the device 2020. That is, as depicted in FIG. 9, "40 lx" as the illuminance limitation value 703 (an example of the first value) corresponding to the sleep state 701 being "NREM3" is set as illuminance upper limits (property 514) for "television" and "lighting device" of "2F main bedroom".

The operation limiting unit 2003 corrects the sound volume limitation value 702 (FIG. 7) in the limitation information 700 with the soundproof performance value 602 (FIG. 6) in the soundproof performance information 600, and sets an obtained corrected value (an example of the first value) as a sound volume upper limit (property 516 of FIG. 9) of the device 2020.

For example, "30 dB" as the sound volume limitation value 702 corresponding to the sleep state 701 being "NREM3" is corrected with "0 dB" as the soundproof performance value 602 of "2F main bedroom", and the sound volume upper limit (property 516) for "television" in "2F main bedroom" is set at "30 dB" as depicted in FIG. 9.

Also, for example, "30 dB" as the sound volume limitation value 702 corresponding to the sleep state 701 being "NREM3" is corrected with "−10 dB" as the soundproof performance value 602 of "1F living room", and the sound volume upper limit (property 516) for "television" in "1F living room" is set at "40 dB" as depicted in FIG. 9.

(Operation)

Figure 10:
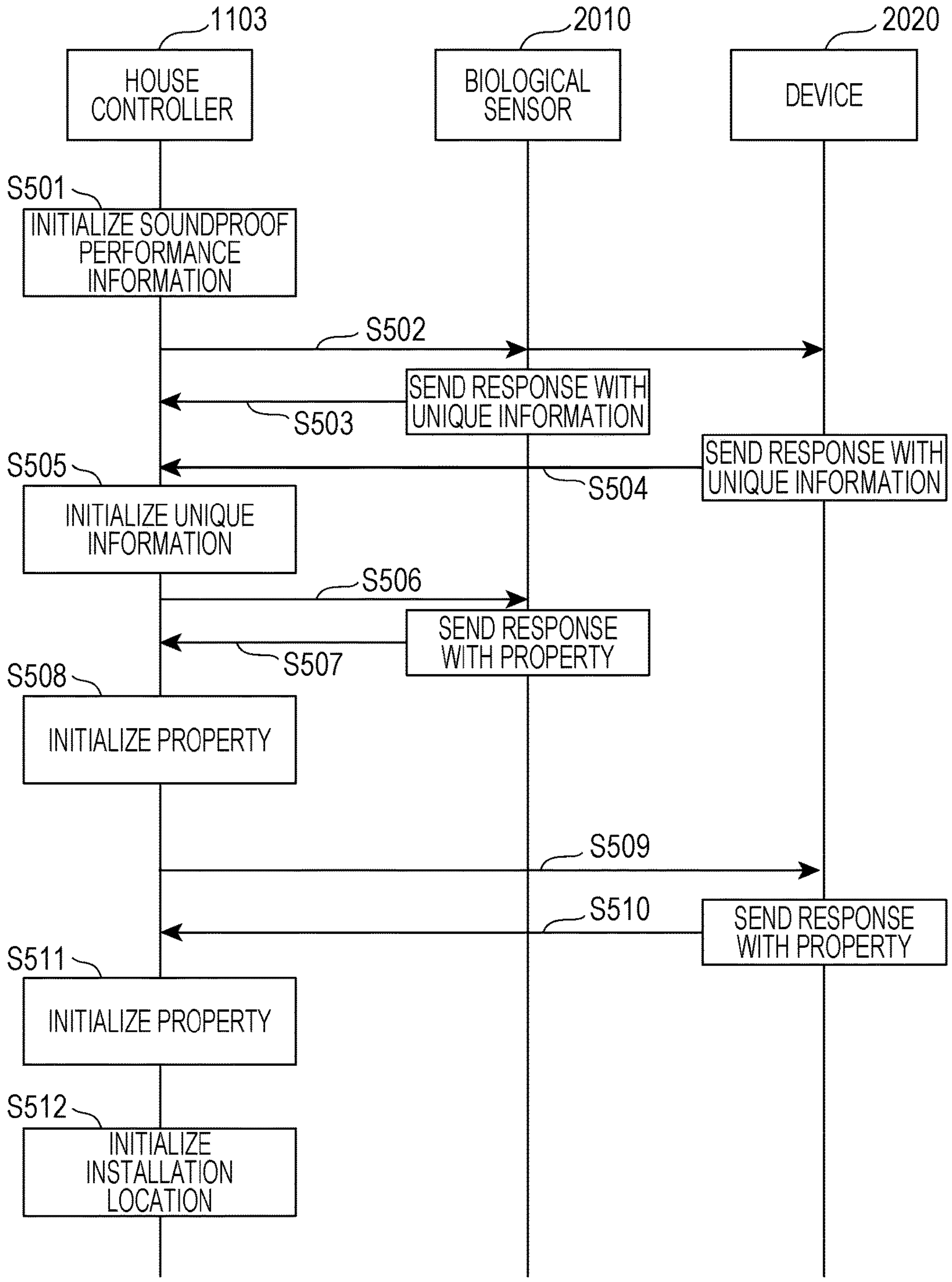
FIG. 10 is a diagram of an initial operation sequence of the device control system in the first embodiment.

FIG. 10 is a sequence diagram schematically depicting initial operation of the device control system in the first embodiment. At first startup, the house controller 1103 initializes the soundproof performance information 600 in the room DB 2007 and initializes the device management information 500 in the device DB 2005.

At step S501, based on the input by the user, the room managing unit 2006 of the house controller 1103 sets an initial value of the soundproof performance value 602 in the soundproof performance information 600. Note that a default value set by a housing manufacturer may be used as an initial value of the soundproof performance value 602 in the soundproof performance information 600.

Subsequently, at step S502, the device managing unit 2004 of the house controller 1103 multicasts a device search request onto the network. Upon receiving the device search request, the biological sensor 2010 sends a response with unique information at step S503, and the device 2020 sends a response with unique information at step S504.

The unique information includes the device ID 501, the IP address 502, the device class 503, the identifier 504, and the number of properties in the device management information 500 (FIG. 5). Since the biological sensor 2010 has three properties as depicted in FIG. 5, "3" is included in the unique information as the number of properties. When the device 2020 is a television, the number of properties is six as depicted in FIG. 5, and therefore "6" is included in the unique information as the number of properties. When the device 2020 is a lighting device, the number of properties is four as depicted in FIG. 5, and therefore "4" is included in the unique information as the number of properties.

Upon receiving the responses with the unique information from the biological sensor 2010 and the device 2020, at step S505, the house controller 1103 initializes the unique information regarding the biological sensor 2010 and the device 2020 connected to the network (that is, the device ID 501, the IP address 502, the device class 503, and the identifier 504) in the device management information 500.

Next, at step S506, the house controller 1103 requests the biological sensor 2010 to transmit three properties. At step S507, as a response to this request, the biological sensor 2010 transmits the properties to the house controller 1103. At step S508, the house controller 1103 initializes the properties 511 to 513 regarding the biological sensor 2010 in the device management information 500.

Next, at step S509, the house controller 1103 requests the device 2020 to transmit six (or four) properties. At step S510, as a response to this request, the device 2020 transmits the properties to the house controller 1103. At step S511, the house controller 1103 initializes the properties 511 to 516 regarding the device 2020 (in the present embodiment, television and lighting device) in the device management information 500.

Note that since the installation locations of the biological sensor 2010 and the device 2020 are unknown, the property 511 transmitted from the biological sensor 2010 and the device 2020 at step S507 and step S510, respectively, is blank.

Next, at step S512, upon receiving the input by the user, the house controller 1103 initializes the installation locations (property 511) of the biological sensor 2010 and the device 2020 in the device management information 500. By the above-described process, initialization of the device management information 500 in the device DB 2005 is completed.

Figure 11:
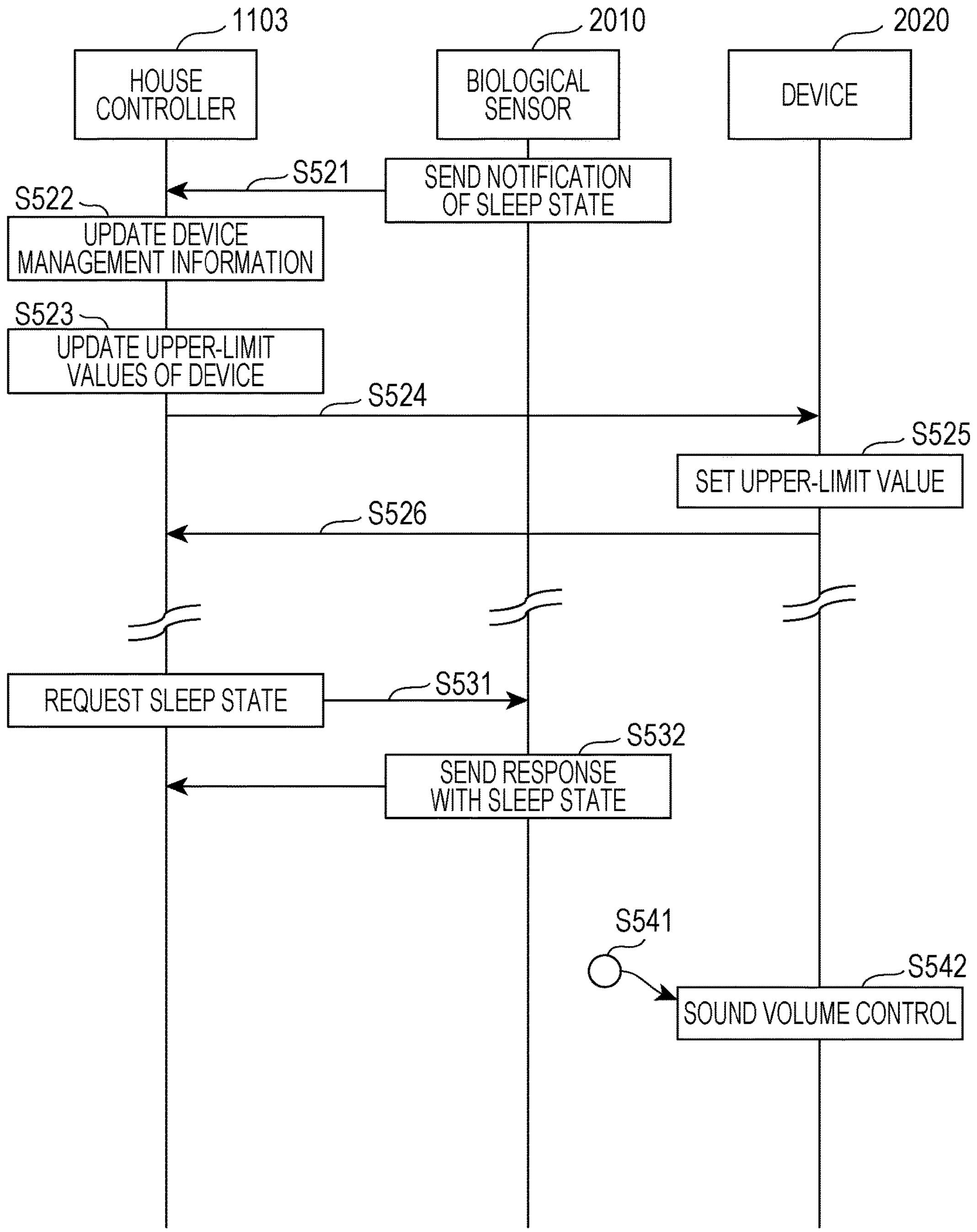
FIG. 11 is a diagram of a normal operation sequence of the device control system in the first embodiment.

FIG. 11 is a sequence diagram schematically depicting normal operation of the device control system in the first embodiment. At step S521, the biological sensor 2010 notifies the house controller 1103 of the sleep state at predetermined time intervals. Note that the biological sensor 2010 may notify the house controller 1103 of the sleep state when the sleep state is changed.

Subsequently, at step S522, the device managing unit 2004 of the house controller 1103 updates the sleep state (property 513) of the device management information 500 stored in the device DB 2005 if the sleep state as notified is changed. In FIG. 11, it is assumed that the sleep state is changed to "NREM3" as depicted in FIG. 9 and the device management information 500 of FIG. 5 is updated to the device management information 500 of FIG. 9.

Subsequently, at step S523, the device managing unit 2004 updates the illuminance upper limit (property 514) and the volume upper limit (property 516) in the device management information 500. Step S523 will be described in detail further below with reference to FIG. 14.

Subsequently, at step S524, via the communication control unit 2008, the device managing unit 2004 requests the device 2020 with its upper-limit value updated (in the present embodiment, for example, television and lighting device) to set an upper-limit value. Upon receiving this request, at step S525, the device 2020 sets an upper-limit value. Step S525 will be described in detail further below with reference to FIG. 12. At step S526 subsequent thereto, the device 2020 notifies the house controller 1103 that the upper-limit value has been set.

Note that if a notification of the sleep state does not come from the biological sensor 2010 to the house controller 1103 even after a predetermined time interval elapses, the house controller 1103 may request the sleep state from the biological sensor 2010 (step S531). As a response to this request, at step S532, the device 2020 may transmit the sleep state (property 513) to the house controller 1103.

At step S525, after the upper-limit value of the device 2020 is set, for example, when the sound volume button is operated by the user (step S541), the audio control unit 2024 of the device 2020 controls the sound volume in accordance with the set upper-limit value (step S542). Step S542 will be described in detail further below with reference to FIG. 13.

Note that while the biological sensor 2010 of the present embodiment has a function of responding to a request for the sleep state from the house controller 1103, this is not meant to be restrictive. For example, the biological sensor may only transmit the sleep state regularly, without a responding function.

Note that the sequence diagram of FIG. 11 represents that processes on an upper side and a lower side that are cut out by wavy lines are performed respectively without being synchronized with each other. The same goes for sequence diagrams hereafter.

Figure 12:
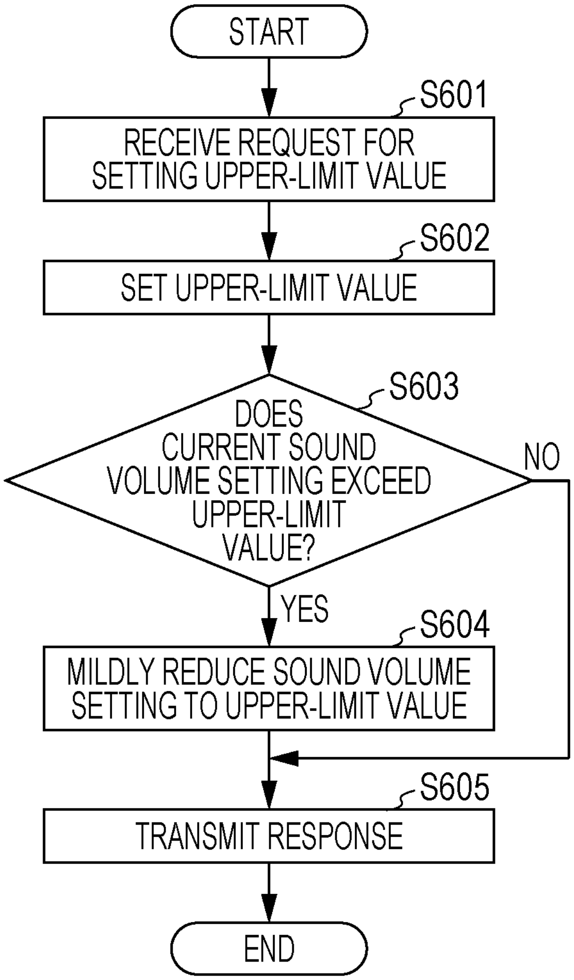
FIG. 12 is a flowchart of details of an upper-limit value setting process in a device.

FIG. 12 is a flowchart of details of an upper-limit value setting process in the device 2020 at step S525 of FIG. 11.

At step S601, the communication control unit 2027 of the device 2020 receives the request (step S524 of FIG. 11) for setting an upper-limit value from the house controller 1103. By following this request, the audio control unit 2024 of the device 2020 sets an upper-limit value (step S602). The audio control unit 2024 retains the set upper-limit value. The audio control unit 2024 may store the set upper-limit value in an internal memory.

Subsequently, at step S603, the audio control unit 2024 determines whether the current sound volume setting exceeds the upper-limit value. When the current sound volume setting exceeds the upper-limit value (YES at step S603), the audio control unit 2024 gradually reduces the sound volume setting over approximately three to five seconds (step S604). The audio control unit 2024 may mildly reduce the sound volume setting at, for example, a rate of change equal to or smaller than 2 dB/second (an example of a predetermined value). Note that while an example of sound volume control is depicted in FIG. 12, illuminance is similarly controlled so as to be gradually reduced.

Subsequently, at step S605, the communication control unit 2027 transmits, to the house controller 1103, a response indicating that the upper-limit value has been set (step S526 of FIG. 11), thereby ending the process of FIG. 12.

Figure 13:
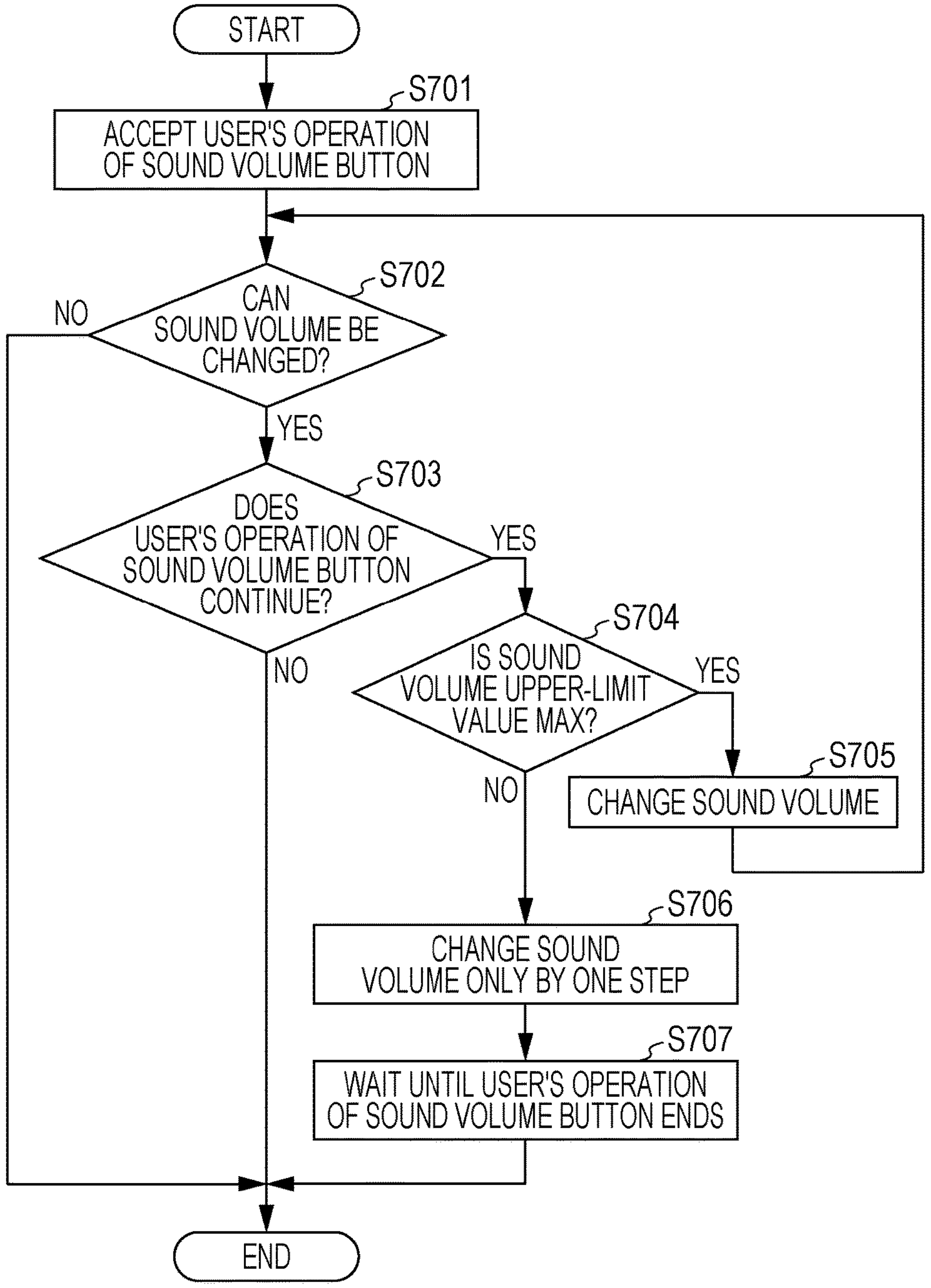
FIG. 13 is a flowchart of details of a sound volume control process in the device.

FIG. 13 is a flowchart of details of a sound volume control process in the device 2020 at step S542 of FIG. 11.

The UI control unit 2026 of the device 2020 accepts operation of the sound volume button from the user, and outputs an operation amount to the data processing unit 2021 (step S701). The audio control unit 2024 determines whether the sound volume can be changed (step S702).

For example, if the current sound volume setting is the upper limit and user's operation of the sound volume button is to increase the sound volume, the audio control unit 2024 determines that the sound volume cannot be changed. Also, if the current sound volume setting is no sound and user's operation of the sound volume button is to reduce the sound volume, the audio control unit 2024 determines that the sound volume cannot be changed. If the sound volume cannot be changed (NO at step S702), sound volume control by following user's operation of the sound volume button cannot be made, and therefore the audio control unit 2024 ends the process of FIG. 13.

If the sound volume can be changed (YES at step S702), the audio control unit 2024 determines, via the UI control unit 2026, whether the user's operation of the sound volume button continues (step S703). If the user's operation of the sound volume button does not continue (NO at step S703), the audio control unit 2024 determines that the user has stopped operation of the sound volume button, and ends the process of FIG. 13.

If the user's operation of the sound volume button continues (YES at step S703), the audio control unit 2024 determines whether the sound volume upper-limit value is at maximum (MAX) (step S704). If the sound volume upper-limit value is MAX, this means that setting an upper-limit value (step S525 of FIG. 11) has not been performed. When the sound volume upper-limit value is MAX (YES at step S704), the audio control unit 2024 changes the sound volume by following the user's operation of the sound volume button (step S705), and the process returns to step S702.

On the other hand, when the sound volume upper-limit value is not MAX (NO at step S704), that is, when setting an upper-limit value has been performed, the audio control unit 2024 changes the sound volume only by one step (step S706), waits until the user's operation of the sound volume button ends (step S707), and then ends the process of FIG. 13. By the processes at step S706 and step S707, even if the user is continuously operating the sound volume button, the sound volume is changed only by one step. That is, the user can change the sound volume only by one step. With this, the sound volume is mildly changed. As a result, sleeper's sleep can be prevented from being interrupted by a change in sound volume.

Figure 14:
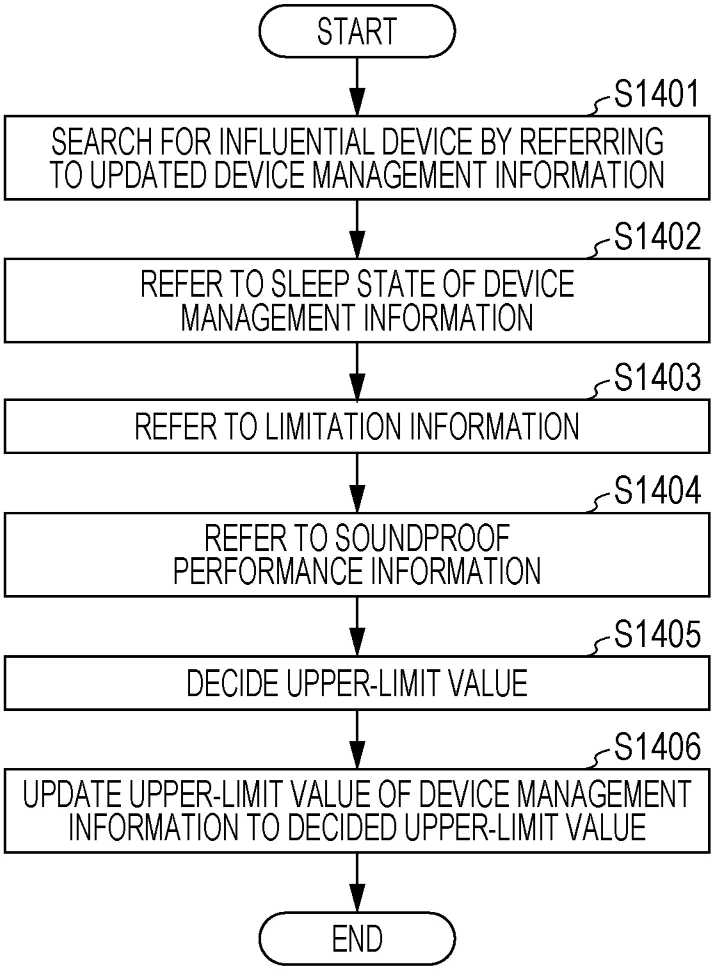
FIG. 14 is a flowchart of details of an upper-limit value updating process in a house controller.

FIG. 14 is a flowchart of details of an upper-limit value updating process at step S523 of FIG. 11.

First, at step S1401, the device managing unit 2004 refers to the updated device management information 500 to search for any influential device 2020 with respect to the installation location of the biological sensor 2010 (property 511). All devices which generate sound (for example, televisions) are influential devices, and a device which generates only light without generating sound (for example, a lighting device) is an influential device if the device is installed at the same location. In the device management information 500 of FIG. 9, influential devices with respect to the installation location of the biological sensor 2010 (that is, 2F main bedroom where the sleeper with the sleeping state being "NREM3" is present) are "television" and "lighting device" in "2F main bedroom" and "television" in "1F living room".

When any influential device (in the present embodiment, the televisions and the lighting device described above) are found, the device managing unit 2004 refers to the sleep state (property 513) in the device management information 500 (step S1402, an example of a sleep state referring step), refers to the limitation information 700 (step S1403), and refers to the soundproof performance information 600 in the room DB 2007 (step S1404, an example of a soundproof performance referring step).

At step S1405 subsequent thereto, the device managing unit 2004 decides an upper-limit value (an example of a deciding step). For example, when the sleep state (property 513) in the device management information 500 is "NREM3", the device managing unit 2004 extracts "30 dB" corresponding to "NREM3" as the sound volume limitation value 702, and extracts "40 lx" corresponding to "NREM3" as the illuminance limitation value 703, from the limitation information 700.

The device managing unit 2004 decides an illuminance upper-limit value of "television" and "lighting device" in "2F main bedroom" as "40 lx" extracted as the illuminance limitation value 703.

The device managing unit 2004 decides a sound volume upper-limit value of "television" in "2F main bedroom" as "30 dB" extracted as the sound volume limitation value 702, because the soundproof performance value 602 in the soundproof performance information 600 is "0 dB".

The device managing unit 2004 decides a sound volume upper-limit value of "television" in "1F living room" as "40 dB" obtained by adding "10 dB" to "30 dB" extracted as the sound volume limitation value 702, because the soundproof performance value 602 in the soundproof performance information 600 is "−10 dB".

At step S1406 subsequent thereto, the device managing unit 2004 updates the illuminance upper limit (property 514) and the sound volume upper limit (property 516) in the device management information 500 in the device DB 2005 to the decided upper-limit values, and ends the process of FIG. 14.

(Operations and Effects)

As has been described above, according to the first embodiment, the house controller 1103 refers to the sleep state of the sleeper determined by the biological sensor 2010. The house controller 1103 decides a sound volume upper-limit value of the device 2020 in accordance with the sleep state of the sleeper. With this, the user (an example of a non-sleeper) of the device 2020 can use the device 2020 even without grasping the sleep state of the sleeper while reducing influences on the sleeper to keep sleeper's sleep.

Also, in general, the sleeper is prone to react to a rapid increase or decrease in sound volume. By contrast, according to the first embodiment, when operating the sound volume button, the user can change the sound volume only by one step. Therefore, a rapid change in sound volume can be inhibited. As a result, influences on the sleeper can be further decreased.

Modified Embodiment (1) The sound volume control process in the device 2020 at step S542 of FIG. 11 is not restricted to the procedure depicted in FIG. 13.

Figure 15:
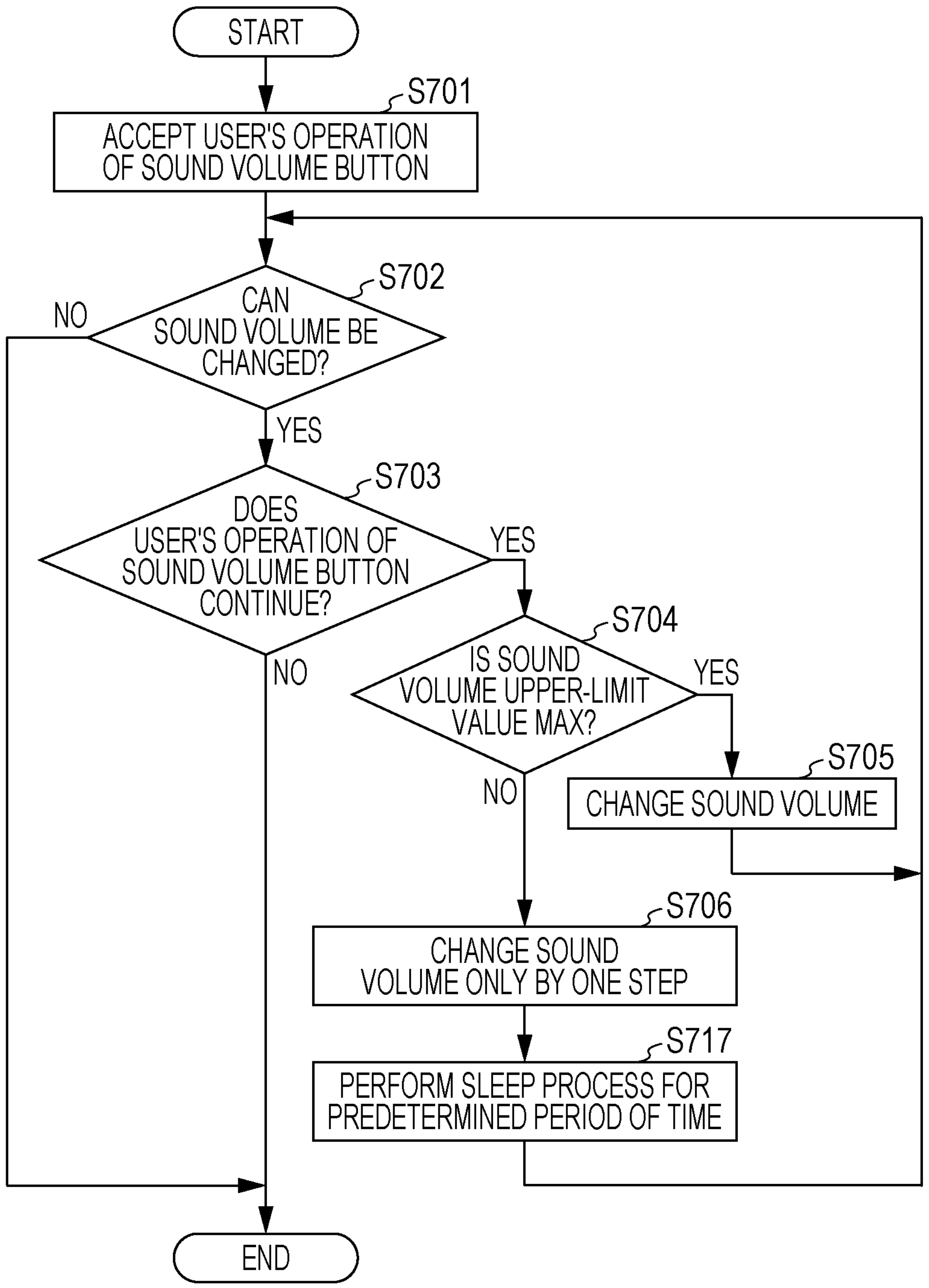
FIG. 15 is a flowchart of details of a sound volume control process different in procedure from those in FIG. 13.

FIG. 15 is a flowchart of a sound volume control process different in procedure from those in FIG. 13. In place of step S707 (wait until the user's operation of the sound volume button ends) of FIG. 13, step S717 is performed in the procedure of FIG. 15. At step S717, the CPU of the device 2020 performs a sleep process for a predetermined period of time. Then, the process returns to step S702. In this structure, a time required for changing the sound volume is extended only by a time during which the sleep process is performed. Thus, effects similar to those of FIG. 13 can be obtained.

(2) The upper-limit-value setting process in the device 2020 at step S525 of FIG. 11 is not restricted to the procedure depicted in FIG. 12.

Figure 16:
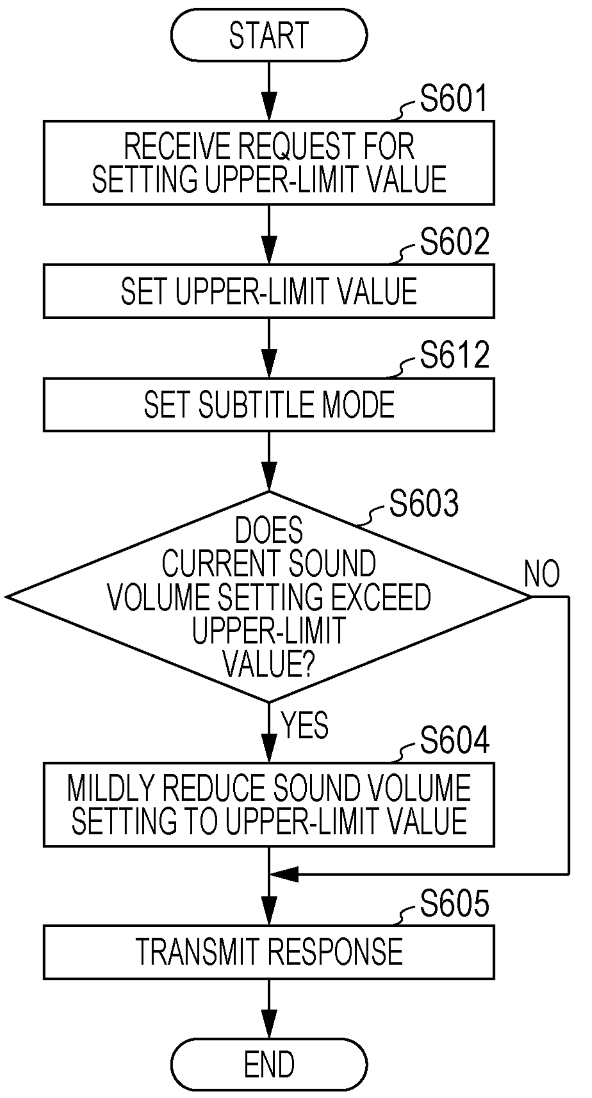
FIG. 16 is a flowchart of details of an upper-limit value setting process different in procedure from those in FIG. 12.

FIG. 16 is a flowchart of details of an upper-limit setting process different in procedure from those in FIG. 12. In the procedure of FIG. 16, subsequently to step S602 (setting an upper-limit value), at step S612, the video control unit 2022 sets a subtitle mode. The subtitle mode is a mode in which video is displayed on the video display unit 2023 with subtitles representing audio. With this, audio with a small sound volume can be complemented, and convenience for a user viewing the device 2020 (television) can be improved.

(3) In FIG. 12, FIG. 13, FIG. 15, and FIG. 16 in the first embodiment, the sound volume is mildly changed by the audio output unit 2025 of the device 2020. However, this is not restricted to a change in sound volume. The video control unit 2022 may also mildly control a change in illuminance by the video display unit 2023 similarly over three to five seconds. Also, when the device 2020 is a lighting device, the lighting control unit may also mildly control a change in illuminance of the electric lamp similarly over three to five seconds. With this, influences of a change in illuminance on the sleeper can be decreased. Also, by mildly changing the sound volume or illuminance, adaptability of the ears or eyes of the user (viewer) of the device 2020 can be ensured. As a result, for sound even with a small sound volume, comfortability to some extent can be ensured. Also, since the room does not get abruptly dark, certain safety can be ensured.

Second Embodiment

In the above-described first embodiment, the operation of setting an upper-limit value of the device 2020 has been described. In a second embodiment, operation of calculating an optimum upper-limit value by using the server 1121 (FIG. 1) and setting the upper-limit value is described. Note that in the following, for simplification of the description, detailed description of structures similar to those of the above-described first embodiment is omitted, with similar reference characters provided.

(Structure)

Figure 17:
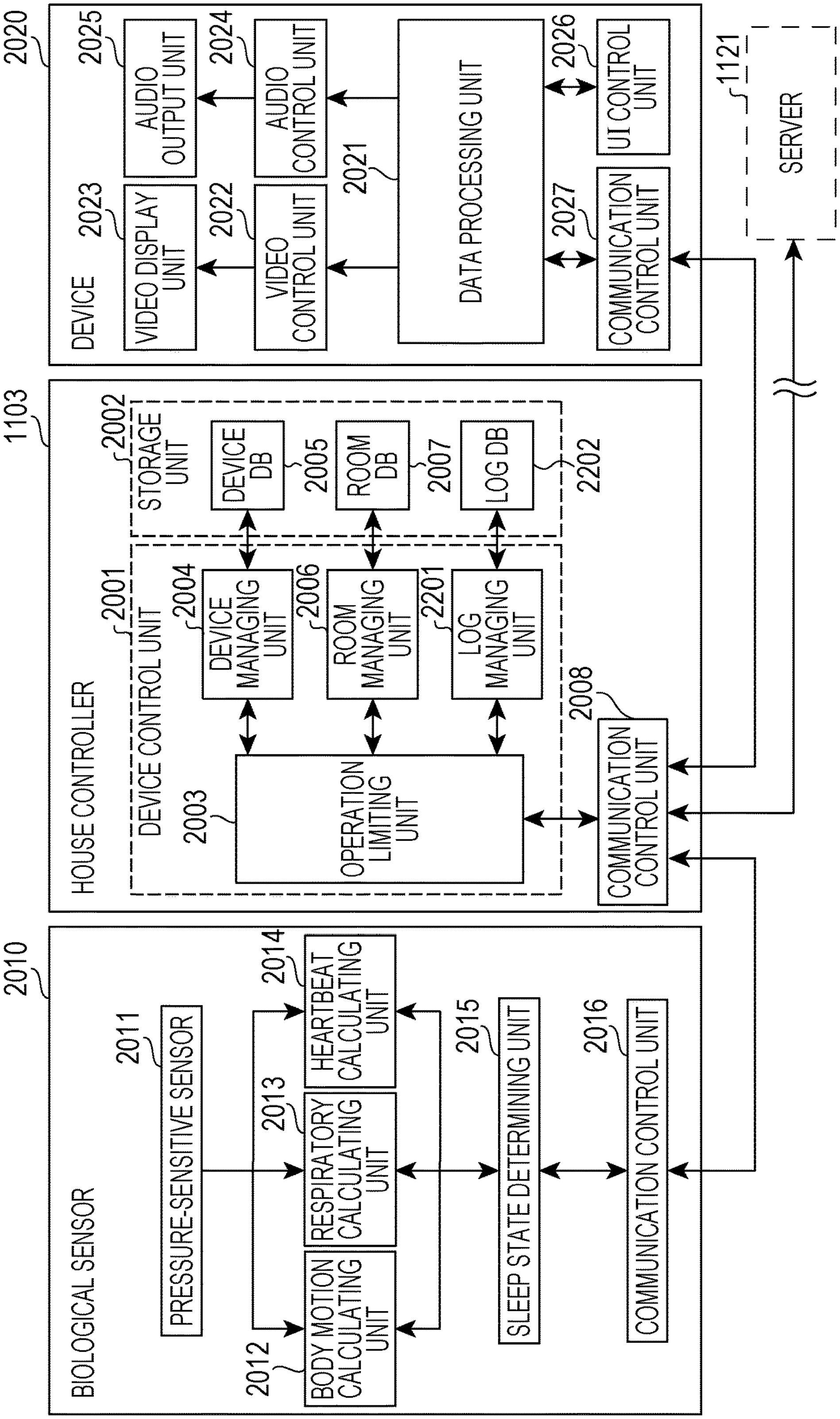
FIG. 17 is a diagram of structure of a device control system in a second embodiment.

FIG. 17 is a block diagram schematically depicting the structure of a device control system according to the second embodiment. As depicted in FIG. 17, the device control unit 2001 of the house controller 1103 includes a log managing unit 2201 in addition to the operation limiting unit 2003, the device managing unit 2004, and the room managing unit 2006. The storage unit 2002 includes a log DB 2202, in addition to the device DB 2005 and the room DB 2007.

The log managing unit 2201 generates log information 1800 (FIG. 18, which will be described further below). The log information 1800 includes an operation log of the device 2020 and a sleep state log of the biological sensor 2010 in a time-series manner. The log managing unit 2201 stores the generated log information 1800 in the log DB 2202.

FIG. 18 is a diagram of an example of the log information 1800 stored in the log DB 2202. As depicted in FIG. 18, the log information 1800 includes a date and time 1801, a device ID 1802, a property number 1803, and a property value 1804.

The device ID 1802 is a unique identifier for specifying the device including the device 2020 and the biological sensor 2010. The device ID 1802 corresponds to the device ID 501 in the device management information 500. The property number 1803 indicates the property 513 or 515 in the device management information 500. A property number "3" of FIG. 18 indicates the property 513 (sleep state or illuminance) of FIG. 5, and a property number "5" of FIG. 18 indicates the property 515 (sound volume) of FIG. 5. The property value 1804 indicates a value of the property number 1803. The date and time 1801 indicates a date and time when the value becomes the property value 1804. In this manner, with the log information 1800, the operation log of the device 2020 and the sleep state log of the biological sensor 2010 are managed in a time-series manner.

In the log information 1800 of FIG. 18, a sleep state "NREM3" is determined by the biological sensor 2010 with the device ID 1802 being "Sensor1" at 1:22:00 on Sep. 24, 2015. Then, at 1:23:30, the sound volume of the television with the device ID 1802 being "TV1" is operated to "20 dB". Then, at 1:29:30, the sound volume of that television is increased to "30 dB". At 1:29:40 immediately after the increase in sound volume (after ten seconds from the increase in sound volume), a sleep state "NREM2" is determined by the biological sensor 2010 with the device ID 1802 being "Sensor1". In this manner, in the log information 1800 of FIG. 18, the sleep state is changed from "NREM3" to "NREM2" to become shallow after ten seconds from the increase in sound volume.

Referring back to FIG. 17, the operation limiting unit 2003 of the house controller 1103 transmits, via the communication control unit 2008, the log information 1800 directly to the server 1121 connected via a network or via the cloud server 1111 (FIG. 1).

The server 1121 determines, by data processing such as machine learning, whether the change in sound volume (the increase in sound volume) of the device 2020 by user's sound volume operation and the change of the sleep state determined by the biological sensor 2010 have a correlation. The server 1121 in the second embodiment may be hardware or software such as a learning application.

When determining that the change in sound volume and the change of the sleep state have a correlation, the server 1121 determines that the current soundproof performance value 602 of the soundproof performance information 600 is not appropriate, and corrects the soundproof performance information 600 so that the soundproof performance information 600 includes a more suitable soundproof performance value 602. The server 1121 transmits the correct new soundproof performance information 600 to the house controller 1103.

For example, when a situation in which the sleep state becomes shallow immediately after a change in sound volume occurs a plurality of times, as depicted in the log information 1800 in FIG. 18, the server 1121 determines that the change in sound volume and the change of the sleep state have a correlation. As a result, the server 1121 makes correction of decreasing the soundproof performance value 602 in the soundproof performance information 600. By using FIG. 19 to FIG. 21, correction of the soundproof performance information by the server 1121 is described.

FIG. 19 is a diagram of the device management information 500 when the sleep state is changed from "NREM3" to "NREM2" and the soundproof performance information 600 is not corrected as a comparative example. FIG. 20 is a diagram of an example of the corrected soundproof performance information 600. FIG. 21 is a diagram of the device management information 500 when the sleep state is changed from "NREM3" to "NREM2" and the soundproof performance information 600 is corrected in the present embodiment. In the device management information 500 of FIG. 19, values changed from the device management information 500 of FIG. 9 are underlined. In the device management information 500 of FIG. 21, values different from those in the device management information 500 of FIG. 19 are underlined.

As described above, the device management information 500 when the sleep state is "NREM3" is depicted in FIG. 9. On the other hand, when the sleep state is changed from "NREM3" to "NREM2", as depicted in FIG. 7, the sound volume limitation value 702 is changed from "30 dB" to "25 dB", and the illuminance limitation value 703 is changed from "40 lx" to "30 lx".

Therefore, as depicted in FIG. 19, the property 514 (illuminance upper limit) is changed from "40 lx" to "30 lx" and, as a result, the property 513 (illuminance) is also changed from "40 lx" to "30 lx". Also, the property 516 (sound volume upper limit) of "2F main bedroom" is changed from "30 dB" to "25 dB" and, as a result, the property 515 (sound volume) is also changed from "30 dB" to "25 dB". Furthermore, the property 516 (sound volume upper limit) of "1F living room" is changed from "40 dB" to "35 dB".

When determining that the change in sound volume and the change of the sleep state have a correlation, the server 1121 decreases the soundproof performance value 602 from "2F main bedroom" to "2F main bedroom" from "0 dB" depicted in FIG. 6 to "+1 dB" to correct the soundproof performance value 602 to "+1 dB" as depicted in FIG. 20. With this, the property 516 (sound volume upper limit) of "2F main bedroom" is changed from "25 dB" depicted in FIG. 19 to "24 dB" as depicted in FIG. 21. As a result, the property 515 (sound volume) is also changed from "25 dB" depicted in FIG. 19 to "24 dB" as depicted in FIG. 21.

Whenever determining that the change in sound volume and the change of the sleep state have a correlation, the server 1121 may decrease the soundproof performance value 602 by "+1 dB".

(Operation)

Figure 22:
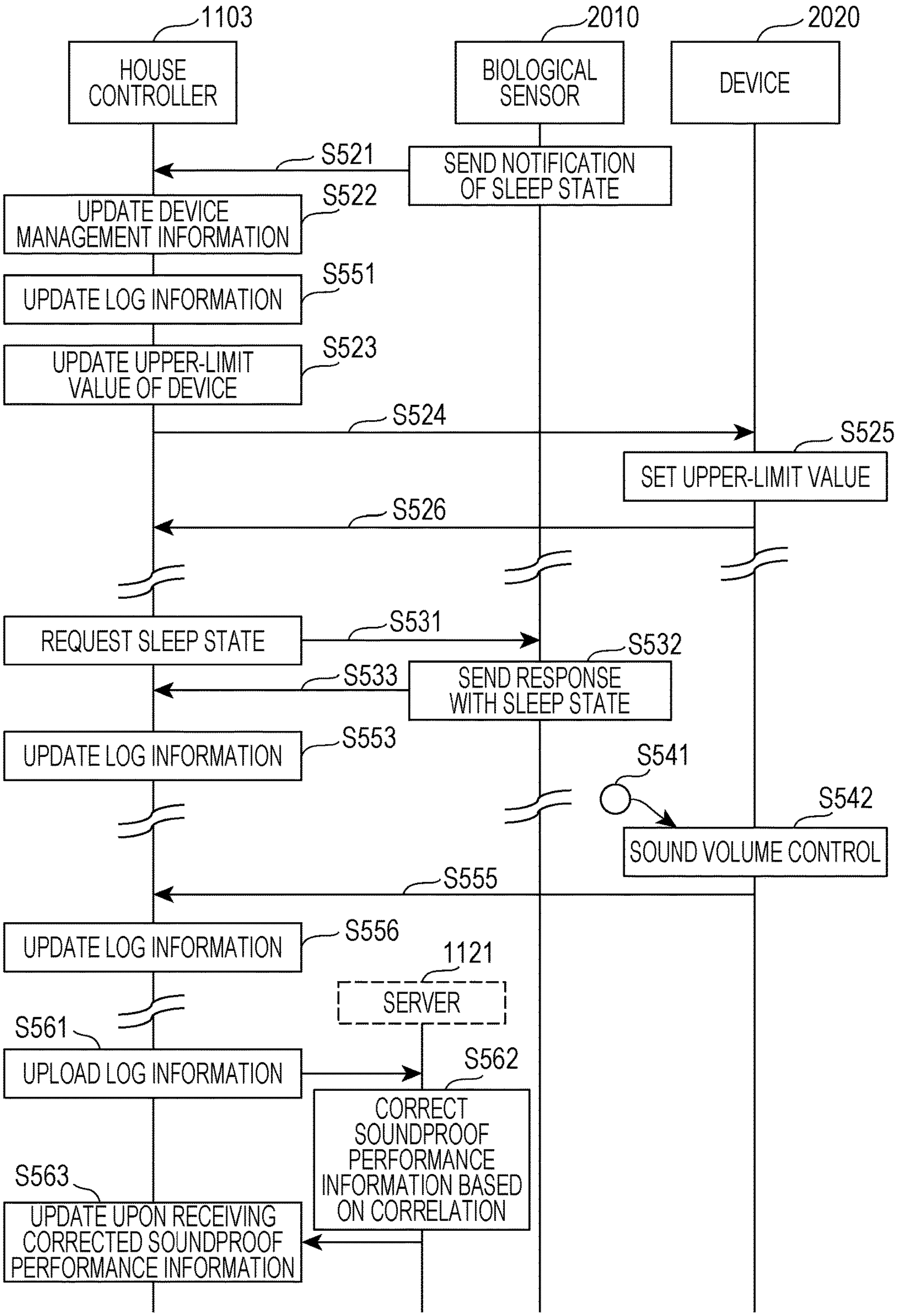
FIG. 22 is a diagram of a normal operation sequence of the device control system in the second embodiment.

FIG. 22 is a sequence diagram schematically depicting normal operation of the device control system. Steps S521 and S522 of FIG. 22 are identical to steps S521 and S522 of FIG. 11. At step S551 subsequent to step S522, the log managing unit 2201 adds the sleep state in the notification at step S521 together with the date and time to the log information 1800 in the log DB 2202 to update the log information 1800. Steps S523 to S526 subsequent thereto are identical to steps S523 to S526 of FIG. 11.

Steps S531 to S533 of FIG. 22 are identical to steps S531 to S533 of FIG. 11. At step S553 subsequent to step S533, the log managing unit 2201 adds the sleep state in the response at step S533 together with the data and time to the log information 1800 in the log DB 2202 to update the log information 1800.

Steps S541 and S542 of FIG. 22 are identical to steps S541 and S542 of FIG. 11. At step S555 subsequent to step S542, the device 2020 notifies the house controller 1103 of the sound volume changed by sound volume control at step S542. Subsequently, at step S556, the log managing unit 2201 adds the sound volume in the notification at step S555 together with the date and time to the log information 1800 in the log DB 2202 to update the log information 1800.

At step S561 of FIG. 22, the house controller 1103 uploads the log information 1800 stored in the log DB 2202, for example, at predetermined time intervals. At step S562, the server 1121 determines whether the change in sound volume and the change of the sleep state have a correlation by, for example, machine learning, and corrects the soundproof performance information 600 based on the determination result. At step S563, upon receiving the corrected soundproof performance information 600, the house controller 1103 updates the soundproof performance information 600 in the room DB 2007. At step S523 subsequent thereto, by using the corrected soundproof performance information 600, the upper-limit value of the device 2020 is updated.

(Operations and Effects)

As described above, for example, when the sound volume of the device 2020 installed in the same room is changed from 20 dB to 30 dB, the sleep state of the sleeper may be changed from non-REM sleep stage 3 (NREM3) to non-REM sleep stage 2 (NREM2). In this case, according to the second embodiment, when it is determined by machine learning that the change in sound volume and the change of the sleep state have a correlation, for example, the soundproof performance value 602 is corrected from 0 dB to +1 dB. With this, the upper-limit value of the sound volume is decreased from 25 dB to 24 dB. As a result, sound influences on the sleeper can be further decreased.

Modified Embodiment (1) In the second embodiment, when it is determined that the change in sound volume and the change of the sleep state have a correlation, the soundproof performance value 602 is decreased by "+1 dB". However, the decrease is not restricted thereto. The soundproof performance value 602 may be decreased by "+2 dB" or "+5 dB", or the decrease in the soundproof performance value 602 may be changed.

(2) In the second embodiment, when it is determined that the change in sound volume and the change of the sleep state have a correlation, the soundproof performance value 602 is decreased. However, this is not meant to be restrictive. When determining that the change in sound volume and the change of the sleep state have a correlation, the server 1121 may directly decrease the value of the property 516 in the device management information 500 of FIG. 21. Also in this case, effects similar to those of the second embodiment can be obtained.

Third Embodiment

In the second embodiment, the operation of calculating an optimum upper-limit value and setting the upper-limit value by using the server 1121 has been described. In a third embodiment, a device control system using a service provider in place of a house controller is described. Note in the following that, for simplification of description, structures similar to those of the first embodiment are provided with a similar reference character and detailed description thereof are omitted.

(Structure)

Figure 23:
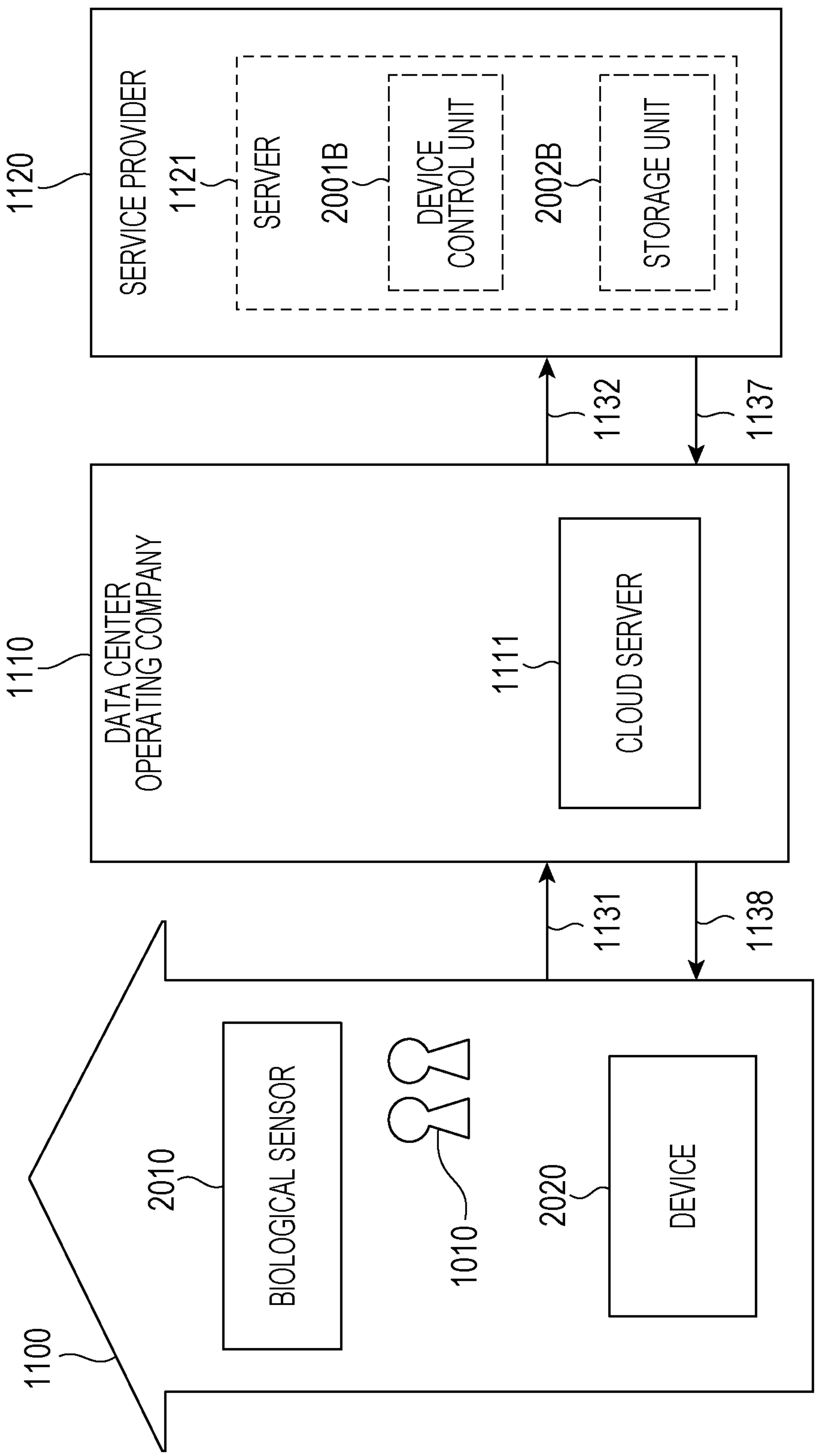
FIG. 23 is a diagram of structure of a device control system in a third embodiment.

FIG. 23 is a diagram schematically depicting the structure of the device control system in the third embodiment. In FIG. 23, the server 1121 has a function as a replacement for the house controller 1103 (FIG. 17) of the second embodiment. The server 1121 has a device control unit 2001B having a function corresponding to the device control unit 2001 depicted in FIG. 17 and a storage unit 2002B having a function corresponding to the storage unit 2002 depicted in FIG. 17. The server 1121 is connected via the cloud server 1111 to the biological sensor 2010 and the device 2020 via a network.

(Operation)

Figure 24:
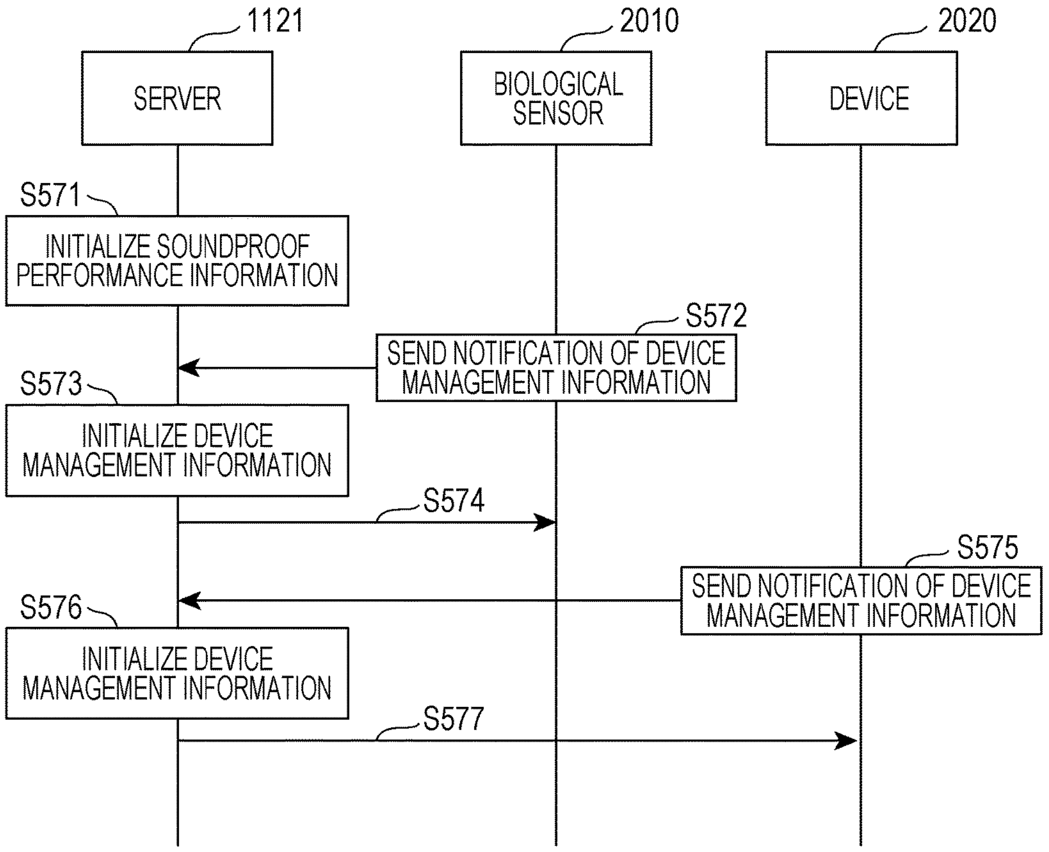
FIG. 24 is a diagram of an initial operation sequence of the device control system in the third embodiment.

FIG. 24 is a sequence diagram schematically depicting initial operation of the device control system in the third embodiment.

At step S571, the device control unit 2001B of the server 1121 sets an initial value of the soundproof performance value 602 in the soundproof performance information 600 (FIG. 6). The device control unit 2001B stores the soundproof performance information 600 with the initial value set therein in the room DB in the storage unit 2002B. As an initial value of the soundproof performance value 602 in the soundproof performance information 600, a default value set by a housing manufacturer is used. Note that the initial value of the soundproof performance value 602 in the soundproof performance information 600 may be set, for example, by the user 1010 by using the device 2020.

At step S572, the biological sensor 2010 transmits the items 501 to 504 and 511 to 513 in the device management information 500 (FIG. 5) to the server 1121 to request registration of the device (arrows 1131 and 1132 in FIG. 23).

At step S573, the device control unit 2001B of the server 1121 registers the transmitted device management information 500 regarding the biological sensor 2010 in the device DB in the storage unit 2002B. With this, the device management information 500 regarding the biological sensor 2010 is initialized. Note that the biological sensor 2010 may have a function of allowing the user 1010 to set its installation location. The biological sensor 2010 may transmit information set by the user 1010 to the server 1121 as the property 511 (installation location) of the device management information 500.

At step S574, the server 1121 transmits, to the biological sensor 2010, a response indicating that devise registration has been completed.

At step S575, the device 2020 transmits the items 501 to 504 and 511 to 516 in the device management information 500 (FIG. 5) to the server 1121, to request registration of the device (arrows 1131 and 1132 in FIG. 23).

At step S576, the device control unit 2001B of the server 1121 registers the transmitted device management information 500 regarding the device 2020 in the device DB in the storage unit 2002B. With this, the device management information 500 regarding the device 2020 is initialized. Note that the device 2020 may have a function of allowing the user 1010 to set its installation location. The device 2020 may transmit information set by the user 1010 to the server 1121 as the property 511 (installation location) of the device management information 500.

At step S577, the server 1121 transmits, to the device 2020, a response indicating that devise registration has been completed. By the above-described process, initialization of the device management information 500 is completed.

Next, with reference to FIG. 23, normal operation of the device control system in the third embodiment is described. The biological sensor 2010 notifies the server 1121 of the sleep state at predetermined time intervals (arrows 1131 and 1132). When determining that the sleep state of the biological sensor 2010 is changed, the device control unit 2001B sets, to the device 2020, an upper-limit value suitable for a new sleep state (arrows 1137 and 1138). Note that, here, a push notification type communication may be used for setting from the server 1121 to the device 2020. Alternatively, a change in setting may be achieved by inquiring from the device 2020 to the server 1121 at predetermined time intervals about whether to change setting.

(Operations and Effects)

As described above, according to the third embodiment, in place of the house controller, the server 1121 includes the device control unit 2001B and the storage unit 2002B. Thus, the device control method can be flexibly updated, and an improvement in service quality of the device control system can be further expected.

(Others)

(1) In each of the above-described embodiments, the sound volume setting is gradually reduced over approximately three to five seconds. For example, in FIG. 12, when the current sound volume setting exceeds the upper-limit value (YES at step S603), at step S604, the audio control unit 2024 gradually reduces the sound volume setting over approximately three to five seconds. However, this is not meant to be restrictive.

Figure 25:
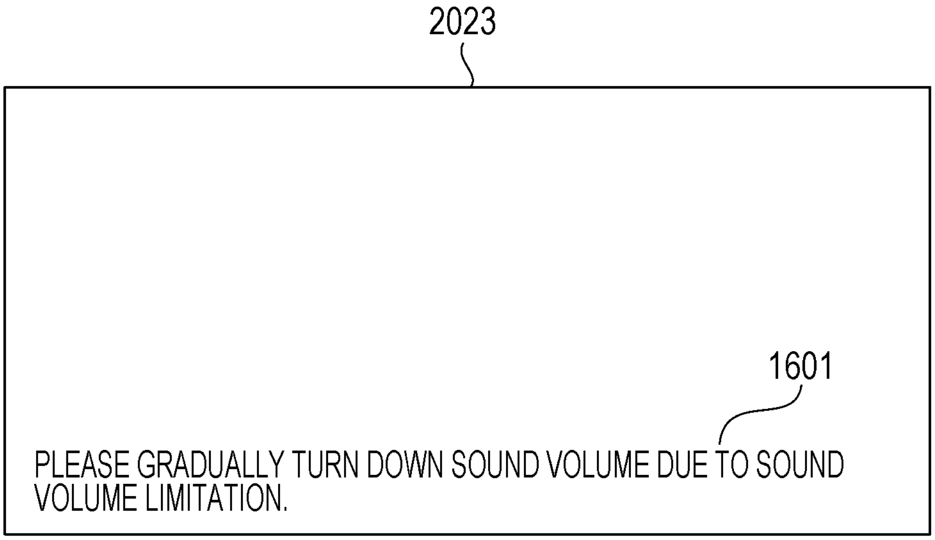
FIG. 25 is a diagram of an example of a message displayed on a video display unit.

FIG. 25 is a diagram of an example of a message displayed on the video display unit 2023. When the current sound volume setting exceeds the upper-limit value, the audio control unit 2024 may generate a message 1601 "Please gradually turn down sound volume due to sound volume limitation." as depicted in FIG. 25. The audio control unit 2024 may notify the video control unit 2022 of the generated message 1601 via the data processing unit 2021. The video control unit 2022 may cause the notified message 1601 to be displayed on the video display unit 2023. By following the message 1601 displayed on the video display unit 2023, the user operates the sound volume button to gradually turn down the sound volume. With this, effects similar to those of each of the embodiments can be obtained.

(2) In each of the above-described embodiments, for example, as depicted in FIG. 9, the house controller 1103 manages the illuminance and sound volume upper limits in the properties 514 and 516 in the device management information 500. Here, for example, when requesting setting of an upper-limit value at step S524 of FIG. 11, the house controller 1103 may transmit an illuminance or sound volume. For example, at step S525 of FIG. 11, the device 2020 receiving the illuminance or sound volume may convert the illuminance or sound volume into an appropriate control value to control the illuminance of the video display unit 2023 or the sound volume of the audio output unit 2025.

Alternatively, for example, at step S524 of FIG. 11, the house controller 1103 may convert the illuminance or sound volume into an appropriate control value and transmit the converted control value. For example, at step S525 of FIG. 11, the device 2020 receiving the control value may use the received control value to control the illuminance of the video display unit 2023 or the sound volume of the audio output unit 2025.

The control value obtained by converting the illuminance or sound volume may be, for example, a current value for controlling the video display unit 2023 or the audio output unit 2025 or a level value simply indicating an illuminance or sound volume level.

Note that the technology described in the above embodiments can be achieved in, for example, cloud service types below. However, the cloud service types where the technology described in the above embodiments is achieved are not meant to be restrictive.

(Service Type 1: In-house Data Center Type Cloud Service)

Figure 26:
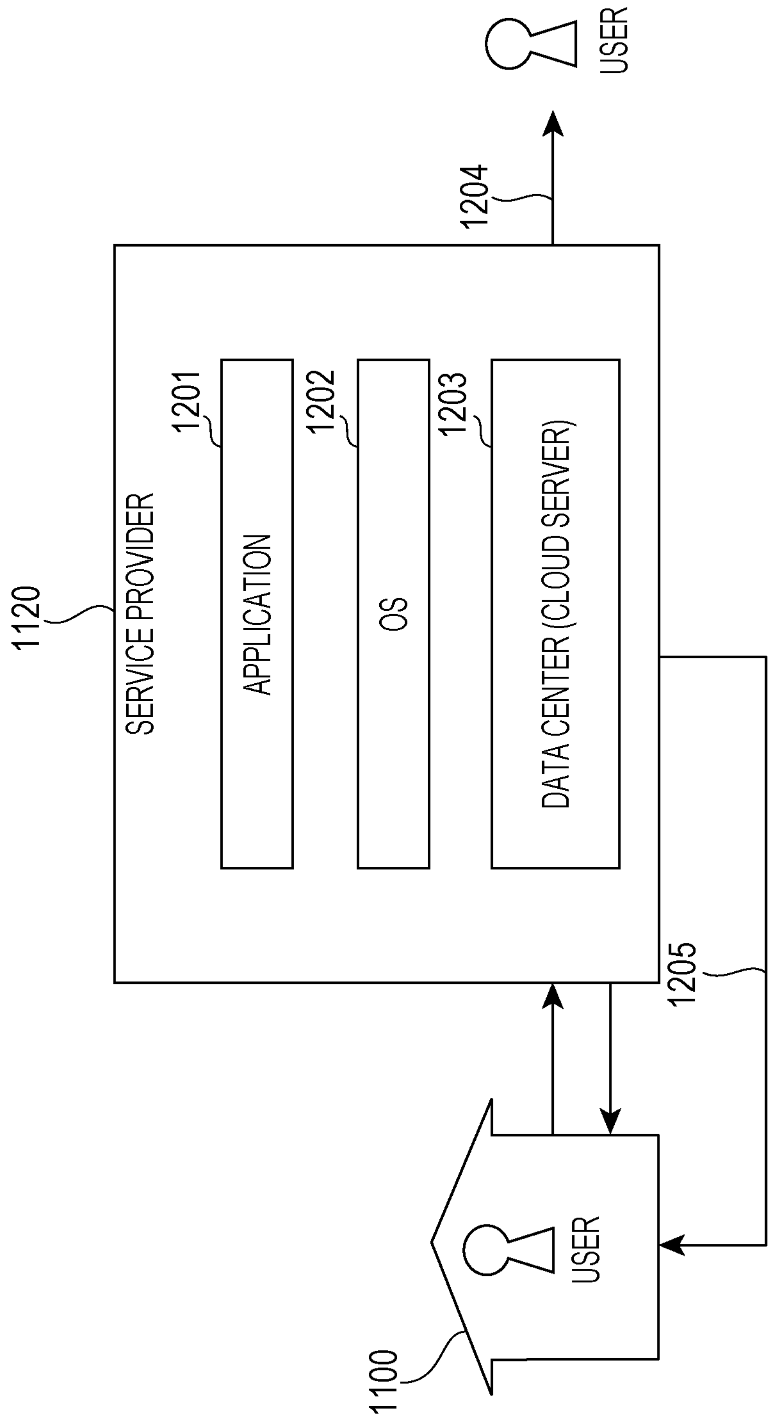
FIG. 26 is a diagram of an overview of service to be provided by the device control system in a service type 1 (in-house data center type cloud service)

FIG. 26 is a diagram of an overview of service to be provided by the device control system in a service type 1 (in-house data center type cloud service). In this type, the service provider 1120 obtains information from the group 1100, and provides service to the group 1100 and the user. In this type, the service provider 1120 has a function of a data center operating company. That is, the service provider 1120 owns the cloud server 1111 which manages big data. Therefore, no data center operating company is present.

In this type, the service provider 1120 operates and manages a data center (cloud server) 1203. Also, the service provider 1120 manages an operating system (OS) 1202 and an application 1201. The service provider 1120 uses the OS 1202 and the application 1201 managed by the service provider 1120 to provide service (arrows 1204 and 1205).

(Service Type 2: IaaS Use Type Cloud Service)

Figure 27:
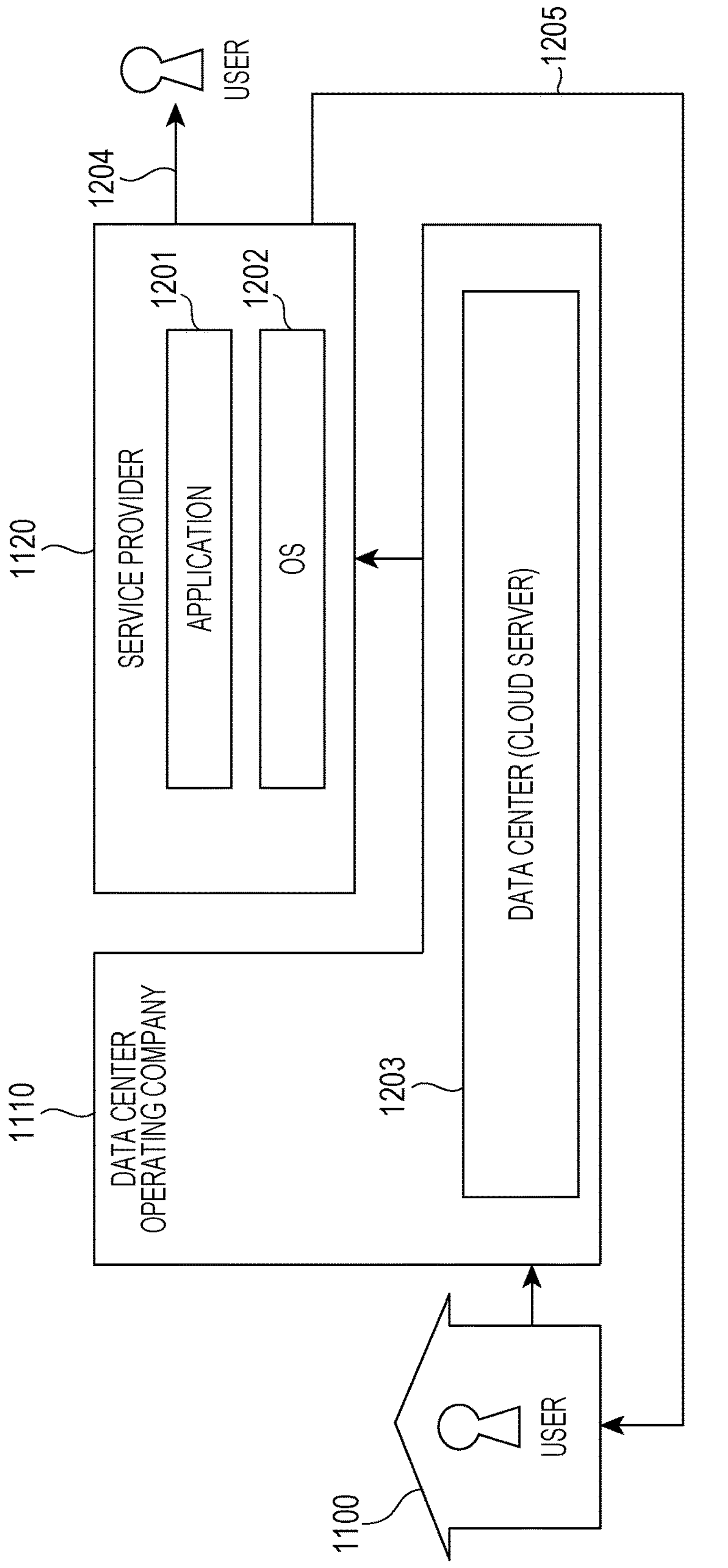
FIG. 27 is a diagram of an overview of service to be provided by the device control system in a service type 2 (IaaS use type cloud service)

FIG. 27 is a diagram of an overview of service to be provided by the device control system in a service type 2 (IaaS use type cloud service). Here, IaaS is an abbreviation of infrastructure as a service, and is a cloud service providing model which provides an infrastructure itself for constructing and operating a computer system as service via the Internet.

In this type, the data center operating company 1110 operates and manages the data center (cloud server) 1203. Also, the service provider 1120 manages the OS 1202 and the application 1201. The service provider 1120 uses the OS 1202 and the application 1201 managed by the service provider 1120 to provide service (arrows 1204 and 1205).

(Service Type 3: PaaS Use Type Cloud Service)

Figure 28:
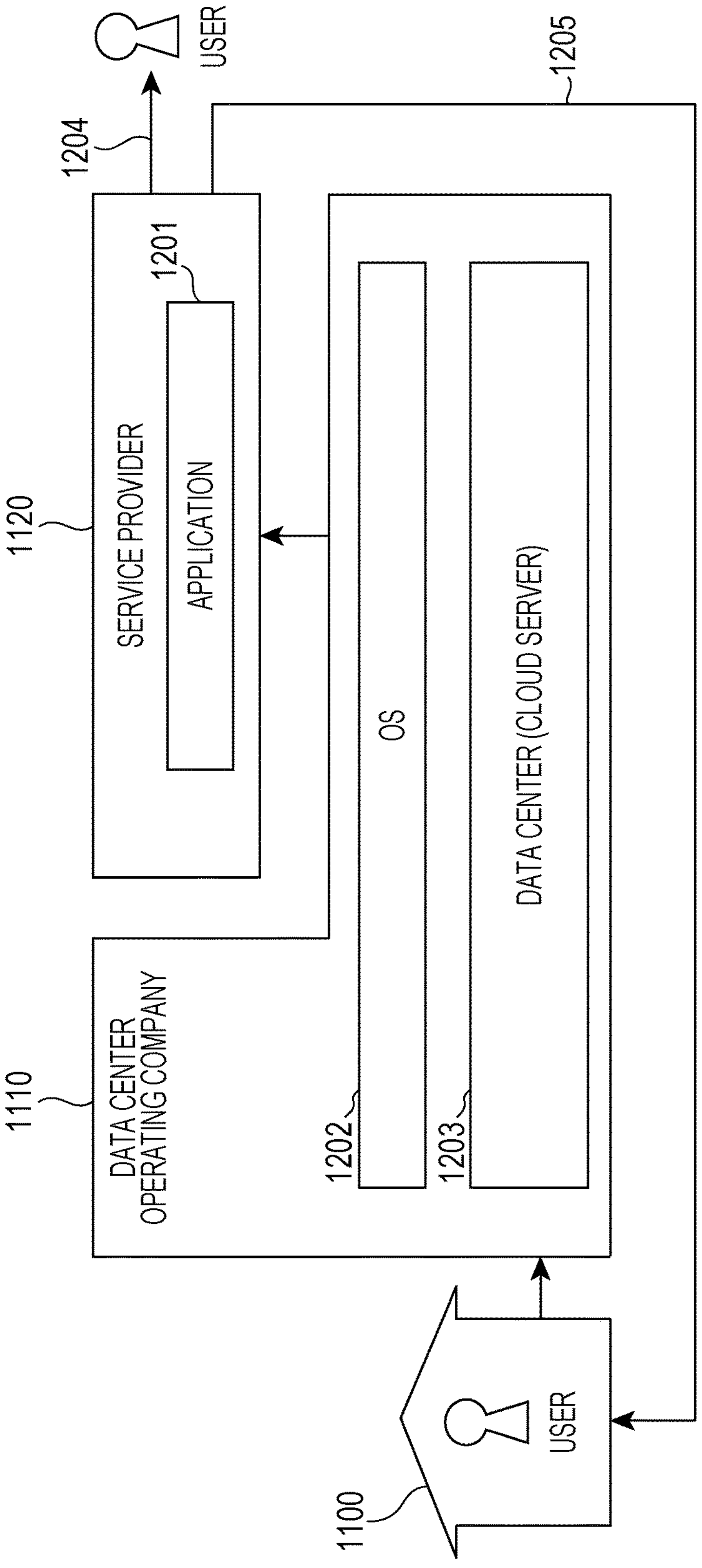
FIG. 28 is a diagram of an overview of service to be provided by the device control system in a service type 3 (PaaS use type cloud service)

FIG. 28 is a diagram of an overview of service to be provided by the device control system in a service type 3 (PaaS use type cloud service). Here, PaaS is an abbreviation of platform as a service, and is a cloud service providing model which provides a platform as a base for constructing and operating software as service via the Internet.

In this type, the data center operating company 1110 manages the OS 1202, and operates and manages the data center (cloud server) 1203. Also, the service provider 1120 manages the application 1201. The service provider 1120 uses the OS 1202 managed by the data center operating company 1110 and the application 1201 managed by the service provider 1120 to provide service (arrows 1204 and 1205).

(Service Type 4: SaaS Use Type Cloud Service)

Figure 29:
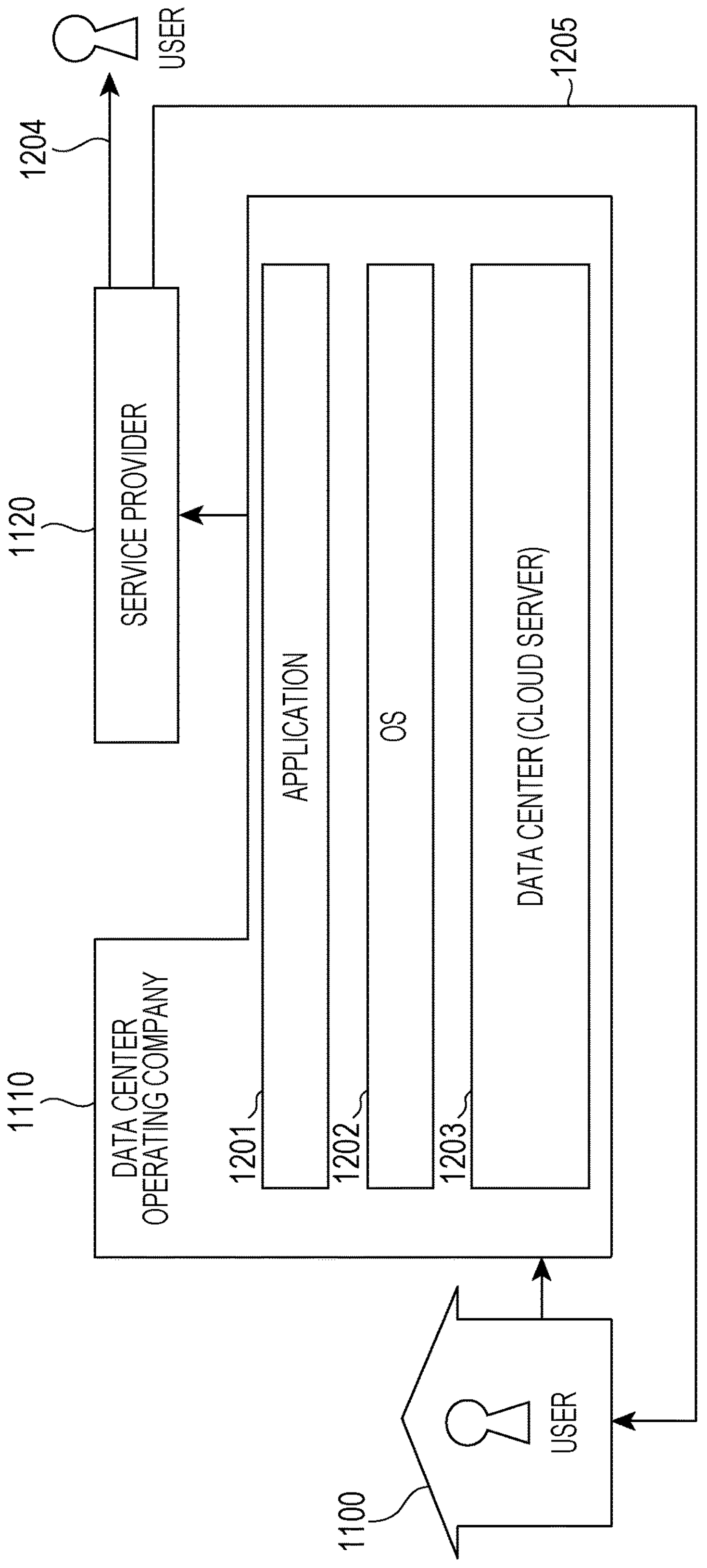
FIG. 29 is a diagram of an overview of service to be provided by the device control system in a service type 4 (SaaS use type cloud service).

FIG. 29 is a diagram of an overview of service to be provided by the device control system in a service type 4 (SaaS use type cloud service). Here, SaaS is an abbreviation of software as a service. For example, the SaaS use type cloud service is a cloud service providing model which has a function of allowing a user such as a company or person not owning a data center (cloud server) to use an application provided by a platform provider who owns a data center (cloud server) via a network such as the Internet.

In this type, the data center operating company 1110 manages the application 1201, manages the OS 1202, and operates and manages the data center (cloud server) 1203. Also, the service provider 1120 uses the OS 1202 and the application 1201 managed by the data center operating company 1110 to provide service (arrows 1204 and 1205).

In the foregoing, in any of the cloud service types, the service provider 1120 provides service. Also, for example, the service provider or the data center operating company may develop an OS, application, database of big data, and so forth by themselves, or may outsource development thereof to a third party.

The control method, controller, and device of the present disclosure are useful for device control when a sleeper and a non-sleeper are both present at home and the non-sleeper uses the device.

What is claimed is:

1. A method of controlling a device located in a predetermined space, the method comprising:
- obtaining sleep information of a person present in a first space from a biological sensor disposed in the first space, the sleep information indicating a sleep state of the person and the first space includes a first device;
- determining, by a processor, a first sound volume to be set for the first device based on the obtained sleep information and a first database indicating a correspondence between the sleep state and a target sound volume of a corresponding device, the target sound volume of the corresponding device being a predetermined sound volume which does not awake a sleeping person at the sleep state and still be heard by an awake person; and
- transmitting, to the first device, a first command for setting the first sound volume in the first device as a sound volume upper-limit value.

2. The method according to claim 1, wherein
- the first database further indicates a correspondence between the sleep state and a target illuminance level of the corresponding device, and
- the method further comprising:
  - determining, by the processor, a first illuminance level of the first device based on the obtained sleep information and the first database, and
  - transmitting, to the first device, a second command for setting the first illuminance level in the first device as an illuminance upper-limit value, the target illuminance level of the corresponding device being a predetermined illuminance level which does not awake the sleeping person at the sleep state while providing visibility for the awake person.

3. The method according to claim 1, further comprising:
- determining, by the processor, a second sound volume of a second device located in a second space based on the obtained sleep information, the first database, and a second database indicating a reduction amount of sound when the sound is transmitted from the second space to the first space, the second sound volume being smaller than the first sound volume; and
- transmitting, to the second device, a third command for setting the second sound volume in the second device as a sound volume upper-limit value.

4. The method according to claim 1, wherein
- the biological sensor is attached to the person.

5. The method according to claim 1, wherein
- the first space includes a bedroom.

6. The method according to claim 5, wherein
- the biological sensor includes a vibration sensor installed in a bedding disposed in the bedroom.

7. The method according to claim 5, wherein
- the biological sensor includes a radio sensor inside a bedding disposed in the bedroom or installed in a predetermined range from the bedding.

8. The method according to claim 1, wherein
- the biological sensor measures a body motion, a respiration rate, and a heart rate of the person, and
- the sleep information is calculated based on a number of times the person turns-over per unit time calculated from the body motion, the respiration rate of the person, and the heart rate of the person.

9. The method according to claim 1, further comprising:
- storing sleep log information in a memory, the sleep log information indicating a correspondence between the sleep state and a corresponding date,
- storing operation log information in the memory, the operation log information indicating a correspondence between a history of changing a sound volume of the first device and a corresponding date,
- determining, by the processor, based on the sleep log information and the operation log information, whether the sleep state indicated in the sleep information becomes shallow after increasing the sound volume of the first device, and
- correcting the first database when it is determined by the processor that the sleep state indicated in the sleep information becomes shallow a predetermined number of times or more after the increasing the sound volume of the first device.

10. The method according to claim 3, further comprising:
- storing sleep log information in a memory, the sleep log information indicating a correspondence between the sleep state and a corresponding date;
- storing operation log information in the memory, the operation log information indicating a correspondence between a history of increasing a sound volume of the second device and a corresponding date;
- determining, based on the sleep log information and the operation log information, whether the sleep state indicated in the sleep information becomes shallow after increasing the sound volume of the second device; and
- correcting the second database when it is determined by the processor that the sleep state indicated in the sleep information becomes shallow a predetermined number of times or more after the increasing the sound volume of the second device.

11. A method of controlling a device included in a predetermined space, the method comprising:
- receiving, from a processor, a first command for setting a first sound volume in the device as a sound volume upper-limit value; and
- setting, by the processor, the first sound volume as the sound volume upper-limit value in the device, wherein the first sound volume is determined by the processor based on a database and sleep information of a person present in the predetermined space, the sleep information being obtained from a biological sensor disposed in the predetermined space, the sleep information indicates a sleep state of the person, the database indicates a correspondence between the sleep state and a target sound volume of a corresponding device, and the target sound volume of the corresponding device is a predetermined sound volume which does not awake a sleeping person at the sleep state and still be heard by an awake person.

12. The method according to claim 11, further comprising:

receiving, from the processor, a second command for setting a first illuminance level in the device as an illuminance upper-limit value; and setting the first illuminance level in the device as the illuminance upper-limit value, wherein the database further indicates a correspondence between the sleep state and a target illuminance level of a corresponding device, the first sound volume is determined by the processor based on the sleep information and the database, and the target illuminance level of the corresponding device is a predetermined illuminance level which does not awake the sleeping person at the sleep state while providing visibility for the awake person.

13. The method according to claim 11, further comprising:

determining, by the processor, whether a second sound volume, which is a volume setting different from the first sound volume, exceeds the first sound volume that is set as the sound volume upper-limit value; and causing the device to output sound at the first sound volume when it is determined that the second sound volume exceeds the first sound volume.

14. The method according to claim 13, further comprising:

changing a sound volume of the device from the second sound volume to the first sound volume at a predetermined rate of change in a stepwise manner.

15. The method according to claim 11, further comprising:

changing a sound volume of the device to the first sound volume or lower at a predetermined rate of change in a stepwise manner.

16. The method according to claim 11, further comprising:

determining, by the processor, whether a second sound volume, which is a current sound volume of the device, exceeds the first sound volume; and when it is determined that the second sound volume exceeds the first sound volume and the device can replay contents including video and sound with subtitles, causing the device to replay the contents at the first sound volume with the subtitles.

17. The method according to claim 11, wherein the device includes a display, and the method further comprising:

determining whether a second sound volume, which is a current sound volume of the device, exceeds the first sound volume, and causing a notification prompting for decreasing a sound volume of the device in a stepwise manner to be displayed on the display when it is determined that the second sound volume exceeds the first sound volume.

18. A controller which controls a device included in a predetermined space, the controller comprising:

a communicator; and a processor, wherein the communicator obtains sleep information of a person present in the predetermined space from a biological sensor disposed in the predetermined space, the sleep information indicating a sleep state of the person, the processor determines a first sound volume of the device based on a database indicating a correspondence between the sleep state and a target sound volume of a corresponding device, the target sound volume of the corresponding device being a predetermined sound volume which does not awake a sleeping person at the sleep state and still be heard by an awake person, and the communicator transmits, to the device, a command for setting the first sound volume in the device as a sound volume upper-limit value.

19. A device installed in a predetermined space, the device comprising:

a communicator; and a processor, wherein the communicator receives, from a controller connected to the device, a first command for setting a first sound volume in the device as a sound volume upper-limit value, the processor sets the first sound volume as the sound volume upper-limit value in the device, the first sound volume is determined by the controller based on a database and sleep information of a person present in the predetermined space, the sleep information being obtained from a biological sensor disposed in the predetermined space, the sleep information indicates a sleep state of the person, the database indicates a correspondence between the sleep state and a target sound volume of a corresponding device, and the target sound volume of the corresponding device is a predetermined sound volume which does not awake a sleeping person at the sleep state and still be heard by an awake person.

20. The method according to claim 1, wherein wherein the target sound volume corresponding to the first device is a sound volume of the first device in the first space, the sound volume at which the first device does not awake the sleeping person at the sleep state that is in the first space and still be heard by the awake person that is in the first space.

* * * * *